United States Patent [19]
Kato et al.

[11] 4,204,767
[45] May 27, 1980

[54] AUTOMATIC CATAPHORESIS APPARATUS

[75] Inventors: Yutaka Kato, Tama; Hirohiko Tokitoh, Hachioji; Tomohiro Kitahara, Hachioji; Hiromi Ito, Hachioji, all of Japan

[73] Assignee: Olympus Optical Company Ltd., Japan

[21] Appl. No.: 829,957

[22] Filed: Sep. 1, 1977

[30] Foreign Application Priority Data

Sep. 6, 1976 [JP] Japan .................. 51-105719

[51] Int. Cl.² .................................. G01N 21/06
[52] U.S. Cl. .................................. 356/444; 250/561
[58] Field of Search ............... 356/36, 432, 443, 444; 250/561, 571, 569

[56] References Cited

U.S. PATENT DOCUMENTS

| | | | |
|---|---|---|---|
| 3,612,888 | 10/1971 | Boucher | 250/569 |
| 3,994,593 | 11/1976 | Kato et al. | 356/36 |
| 3,999,505 | 12/1976 | Kato et al. | 118/7 |

FOREIGN PATENT DOCUMENTS 2056882  5/1971  Fed. Rep. of Germany.

Primary Examiner—John K. Corbin
Assistant Examiner—R. A. Rosenberger
Attorney, Agent, or Firm—Lerner, David, Littenberg & Samuel

[57] ABSTRACT

An apparatus for automatic cataphoresis comprises means for feeding a blood serum bearing film; a cutter for cutting the film to a given length; means for supplying a buffer solution for wetting the film with a buffer solution; a blood serum applicator including a serum application member, a serum dish assembly, an abutment, a rinsing vessel, a drip mechanism and means for carrying the film; a cataphoresis compartment for forming fractionated patterns of the serum applied to the film; dyeing, decolorizing and drying stations for dyeing, decolorizing and drying the serum bearing film as it is delivered from the cataphoresis compartment; and a densitometer including a vessel of a clearing liquid, a light source and a detector for effecting a colorimetric determination of the serum specimen. In this manner, a determination of a blood serum is automatically achieved by the cataphoretic process.

1 Claim, 40 Drawing Figures

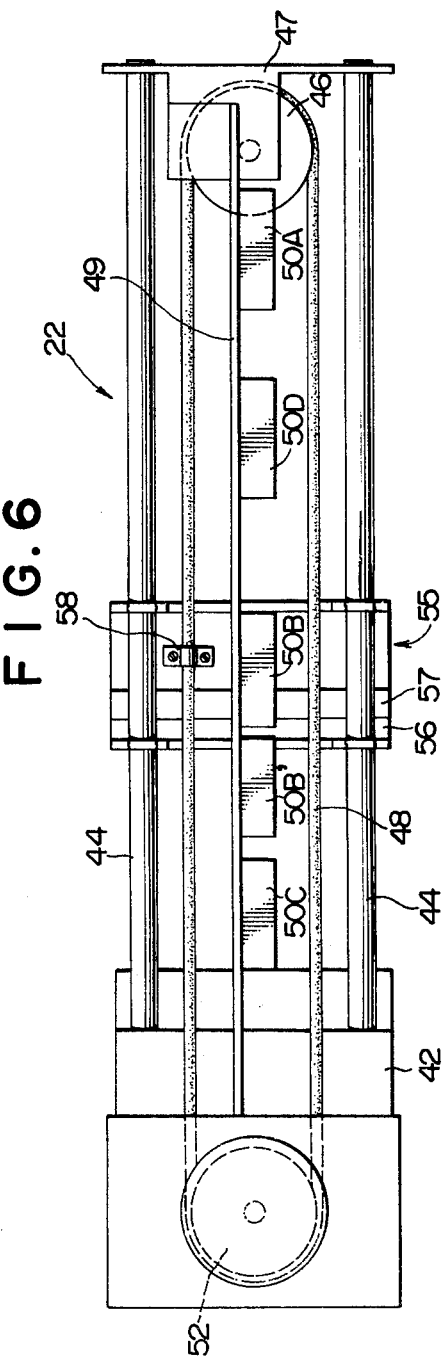
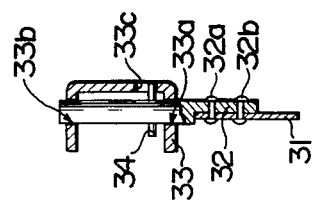
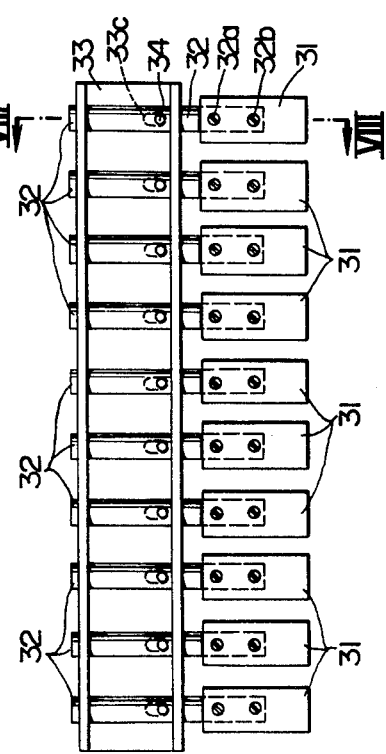

FIG. 9(A) FIG. 9(B) FIG. 10
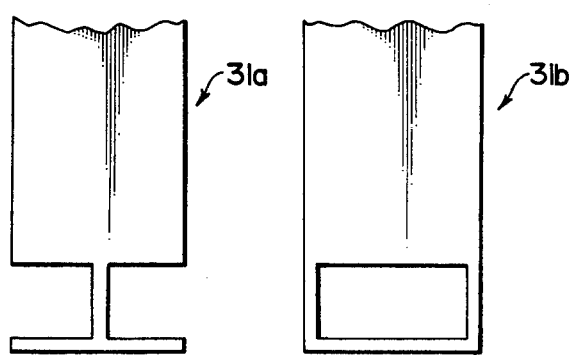
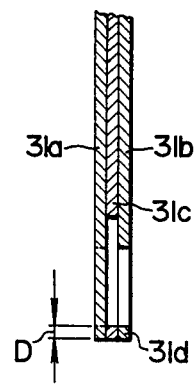
FIG. 11
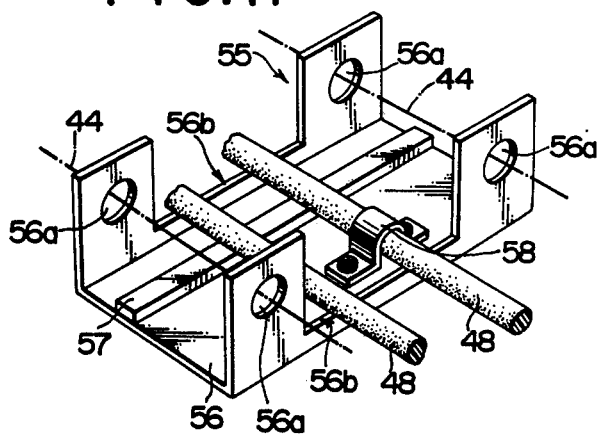
FIG. 12
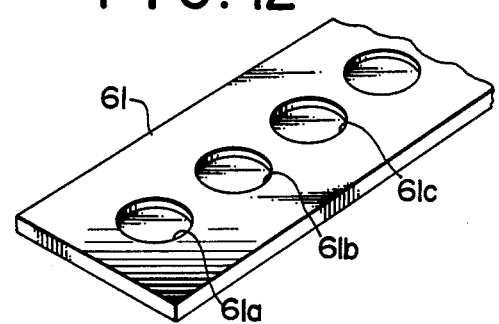

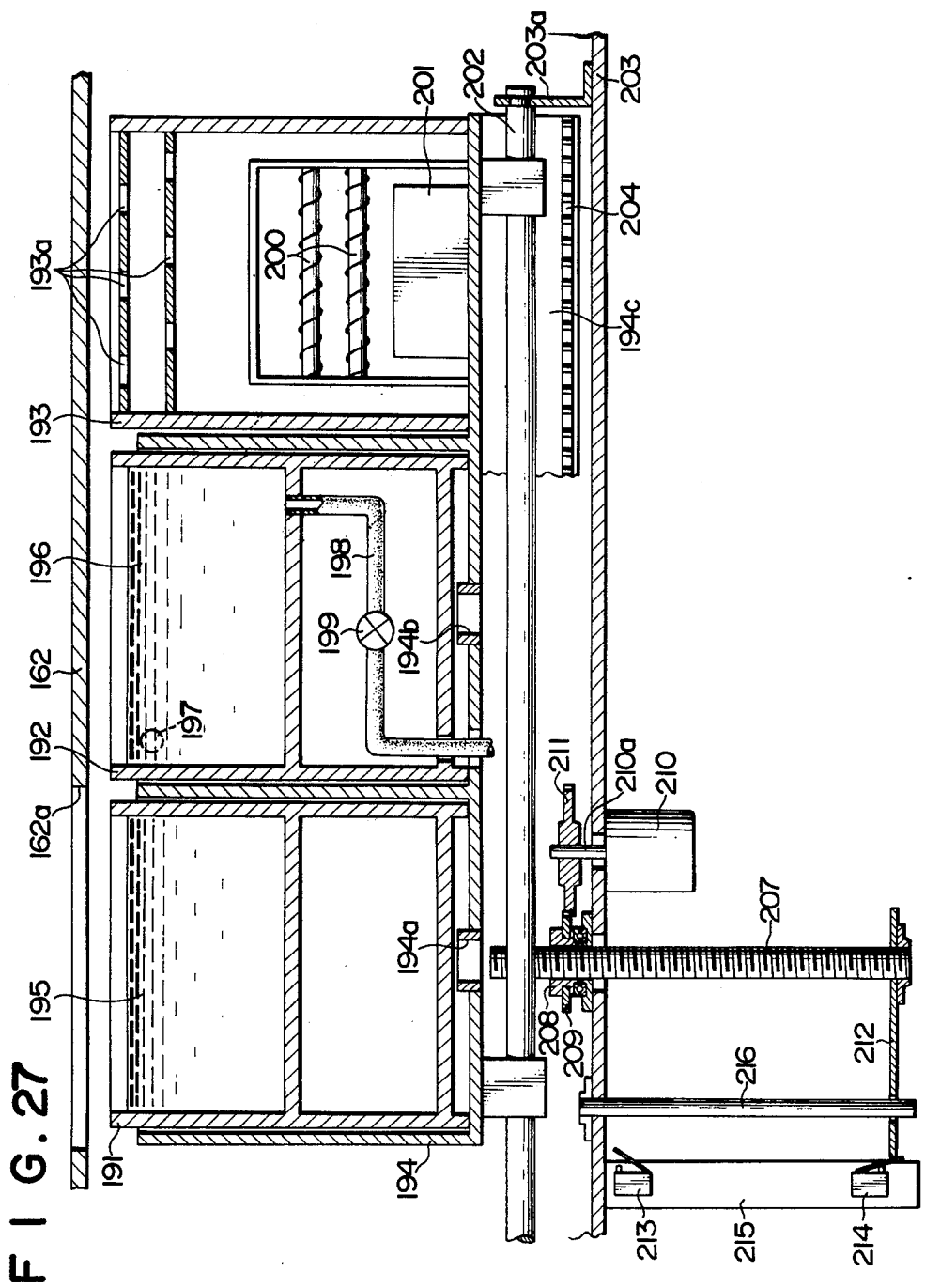

AUTOMATIC CATAPHORESIS APPARATUS

BACKGROUND OF THE INVENTION

The invention relates to an automatic cataphoresis apparatus which permits an examination, by cataphoretic process, of a blood serum to be achieved in an automatic manner.

A cataphoretic process is employed, for example, for the determination of protein contained in a blood serum as in hospitals. The cataphoretic determination comprises the steps of applying a blood serum, by using a pipette, in rectilinear form on the surface of a bearing film which may be formed of a sheet of cellulose acetate, electrically energizing it to form fractionated patterns of a blood serum to be examined, dyeing the film carrying the fractionated patterns of the serum with a dyeing solution comprising, e.g., Ponceau 3R dissolved in a solution of acetic acid trichloride, decolorizing regions of the film other than the fractionated patterns in a solution of acetic acid, drying it, and rendering it clear by immersion in a clearing liquid such as fluid parrafin before conducting a quantitative analysis with a colorimeter. In the prior art practice, all of these steps have been effected manually, resulting in a very inefficient operation. In addition the application of a blood serum to the film requires a high level of skill since an accurate determination result cannot be obtained unless the serum is applied in the form of a thin line of uniform width. In addition, the results obtained may vary from operator to operator even though experienced operators apply the serum. The same applies to other operations of the cataphoretic process beyond the application of the blood serum.

SUMMARY OF THE INVENTION

It is an object of the invention to provide an automatic cataphoresis apparatus which avoids the above disadvantages by enabling an automatic achievement of the various steps of the cataphoretic process in a predetermined sequence.

With the apparatus of the invention, the cataphoretic process is automated throughout the steps of the operation beginning with the step of initially cutting a bearing film from its roll and wetting it to the colorimetric quantitative determination, thus greatly enhancing the operational efficiency. In addition, the automation of various operations permits a uniform and an accurate treatment, which eliminates a variation of the results of determination from operator to operator.

BRIEF DESCRIPTION OF THE DRAWINGS

FIG. 6 is a plan view of a guide member used in the applicator of FIG. 5;

FIG. 7 is a front view of one form of a serum application member;

FIG. 8 is a section taken along the line VIII—VIII shown in FIG. 7.

FIGS. 9(A), 9(B) and 10 are enlarged views illustrating the construction of the penpoint;

FIG. 11 is a perspective view of a carriage for the serum application member;

FIG. 12 is a perspective view of one form of serum dish assembly;

FIGS. 24, 25, 27 and 28 are views, in cross section

DETAILED DESCRIPTION OF PREFERRED EMBODIMENTS

Figure 38:
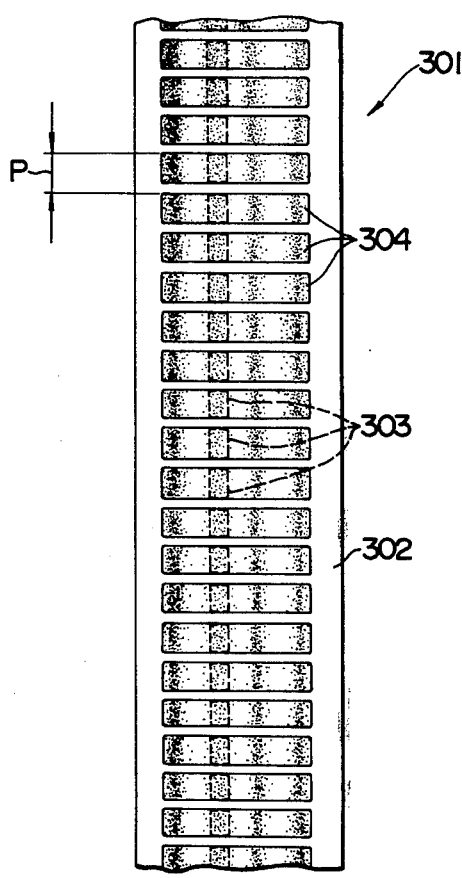
FIG. 38 is a plan view of a serum bearing film.

Referring to FIG. 38, there is shown one example of a specimen film 301. The specimen film 301 is generally produced by a series of steps as mentioned below.

"(1) A carrier film 302 which comprises cellulose acetate is wetted with Veronal-Veronal soda buffer solution.

(2) A blood serum 303 is applied to the carrier film 302 at a given pitch P.

Figure 39:
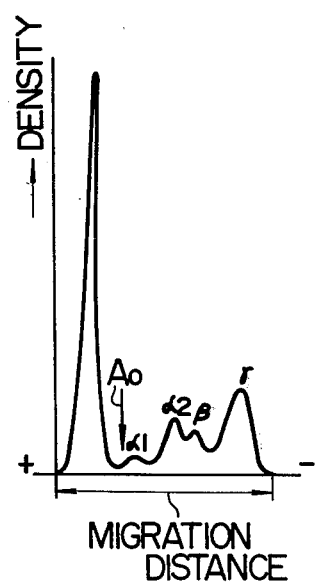
FIG. 39 graphically shows an example of serum analysis on a blood serum bearing film.

(3) A pair of positive and negative electrodes are disposed on the opposite sides of the carrier film, as viewed crosswise thereof, and energized to effect a cataphoresis of the serum 303, which is caused to migrate to produce a fractionated pattern. The direction and the distance of migration of various components contained in the blood serum 303 vary depending on their polarity, and FIG. 39 shows a typical distribution. In FIG. 39, the abscissa represents the distance of migration along the width and the ordinate the density, indicating a density distribution of fractionated components. The peak which is located leftmost represents the density of albumin, which is formed toward the positive electrode relative to the position Ao where the blood serum is applied. Viewing from left to right, successive peaks designated by characters $\alpha_1, \alpha_2, \beta$ and $\gamma$ represent the density of corresponding globulin components, and are formed toward the negative electrode.

(4) The carrier film 302 having the fractionated pattern obtained by the cataphoresis of the serum components is dyed and then decolorized, whereby only the fractionated pattern remains colorized to provide a specimen 304 (see FIG. 3B).

(5) The carrier film 302 having a number of specimens 304 formed thereon is dried to provide a specimen film 301."

The apparatus according to the invention is directed to making the specimen film 301 thus obtained clear by treating it with a clearing liquid and determining the density of the fractionated pattern of respective specimens on the specimen film 301 as by colorimeter on densitometer.

Figure 1:
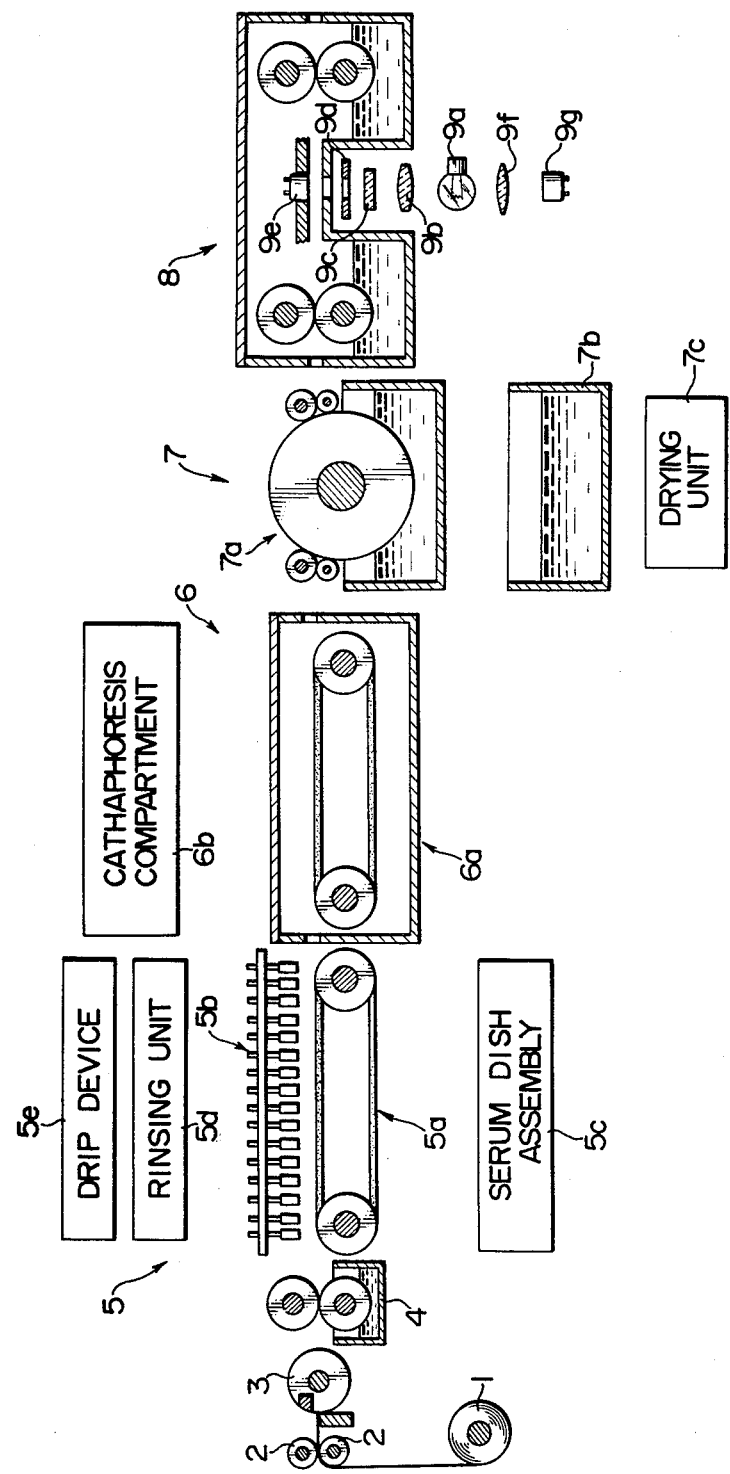
FIG. 1 is a schematic view of the general arrangement of the automatic cataphoresis apparatus according to one embodiment of the invention.

Referring to FIG. 1 the automatic cataphoresis apparatus of the invention is generally shown. Specifically, a blood serum bearing film 1 comprises a sheet of cellulose acetate which is obtained by passing it through the nip of a pair of pulling rollers 2 and cutting it to a given length by a cutter 3, which comprises a stationary and a rotating blade. The film cut is fed to a buffer solution supplying unit 4 in order to immerse it in a buffer solution, which comprises Veronal-Veronal soda solution. After wetting by the unit, the film is then directed to a blood serum applicator 5 which applies a blood serum, a specimen to be examined, onto the wetted film. The applicator comprises a conveyor 5a which conveys the film through an application station 5b, a serum dish assembly 5c, a rinsing vessel 5d and a drip device 5e. When applied with a blood serum, the film is then fed to a cataphoresis station 6 and is electrically energized to form fractionated patterns of the serum. The station 6 comprises a film conveyor 6a and a cataphoresis compartment 6b, and the film carrying the fractionated patterns thereon is supplied to a dyeing, decolorizing and drying station 7 which comprises a dyeing unit 7a, a decolorizing unit 7b and a drying unit 7c. The film is finally fed to a densitometer 8 where a colorimetric determination of the serum is effected. The densitometer includes a supply of clearing liquid, a light source and a detector. The combination of the light source and the detector is constituted by a lamp 9a, condenser lenses 9b, 9f, diffuser 9c, perforated member 9d and light receiving elements 9e, 9g.

Figure 2:
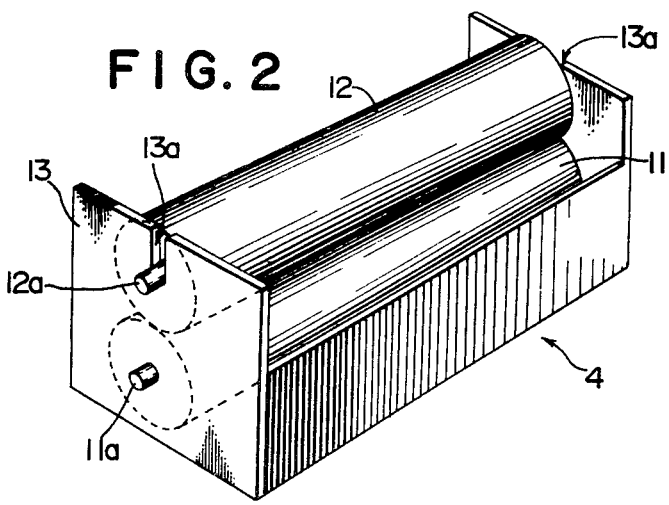
FIG. 2 is a perspective view of one form of a buffer liquid supplying unit.
Figure 3:
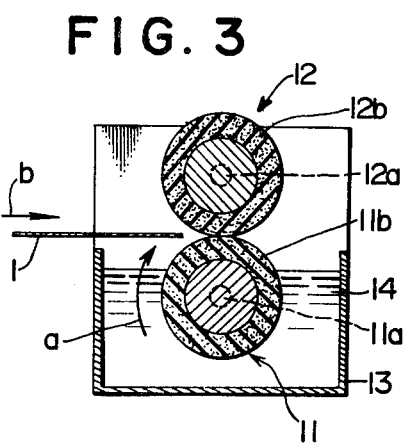
FIG. 3 is a cross section of the unit shown in FIG. 2.

The construction and operation of various units used to perform the steps of the cataphoretic process will be more specifically described. The serum bearing film 1 cut to length is wetted with a buffer solution in the unit 4 before a blood serum is applied thereto in the applicator 5. As shown in FIGS. 2 and 3, the unit 4 comprises a pair of rollers 11, 12 having a surface formed by a hygroscopic material such as sponge, as shown at 11b and 12b. The unit 4 includes a casing 13 in which the shaft 11a of one roller 11 is rotatably mounted. The casing is formed with a groove 13a above the shaft 11a in alignment therewith for receiving the shaft 12a of the other roller 12, which is therefore rotatably mounted. As will be noted from FIG. 3, a buffer solution 14 such as Veronal-Veronal soda solution is contained in the casing 13, and part of the roller 11 is maintained immersed in the buffer solution 14. It is to be understood that the shaft 11a of the roller 11 is driven for rotation by suitable means, not shown. Thus, by passing the film 1 through the nip between the rollers 11, 12 and driving the roller 11 in the direction of an arrow a, the film 1 can be fed from left to right, as shown by an arrow b.

Figure 4:
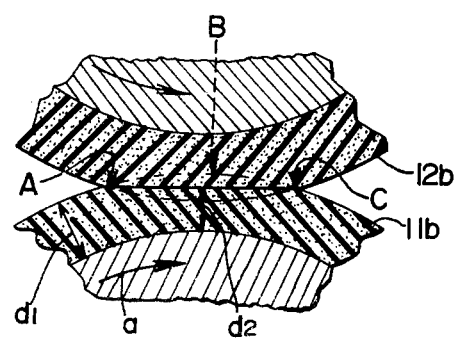
FIG. 4 is a fragmentary enlarged section of the rollers used in the unit of FIGS. 2 and 3.

In operation, when the roller 11 is driven in the direction of the arrow after the film 1 is passed between the rollers 11, 12, the film 1 moves from left to right. Since the roller 12 is partly immersed into the buffer solution 14, the sponge-like surface portion 11b contains the buffer solution. During the movement of the film 1 through the nip between the rollers 11, 12, the buffer solution contained in the roller 11 wets it. Referring to FIG. 4, which illustrates the nip between the rollers to an enlarged scale, the force of gravity exerted on the roller 12 causes a compression of the surface region of both rollers since they are formed of a sponge material. Assuming that the sponge material 11b on the surface of either roller 11 or 12 has a normal thickness $d_1$, the compression causes their thickness to be reduced to a smaller value $d_2$. This means that the buffer solution contained within the surface portion 11b of the roller 11 is squeezed out. In this manner, a sufficient wetting of the film 1 with the buffer solution is assured. However, as both rollers continue to rotate to move past the center B of the mating region, the surface portions of the rollers begin to be restored, and become completely restored at point C where the surfaces of the rollers part. Thus it will be seen that in the region from the center B to point C, the surface portions of both rollers act to absorb any excessive amount of buffer solution from the film. Thus, in the region from point A, where the both rollers begin to contact each other, to point B, the buffer solution contained in the roller 1 is squeezed out to wet the film 1 sufficiently, while any excessive solution is removed therefrom by the absorbing action of the both rollers in the region from point B to point C. While in the example shown, both rollers are provided with surface portions of a sponge material, the sponge surface portion may be provided only on one of the rollers 11 or 12. However, it is found that the provision on sponge surface of the both rollers achieves a more effective removal of any excessive amount of the buffer solution. It should be noted that the compression of the sponge portions may be achieved by other means than the force of gravity acting on roller 12.

Figure 5:
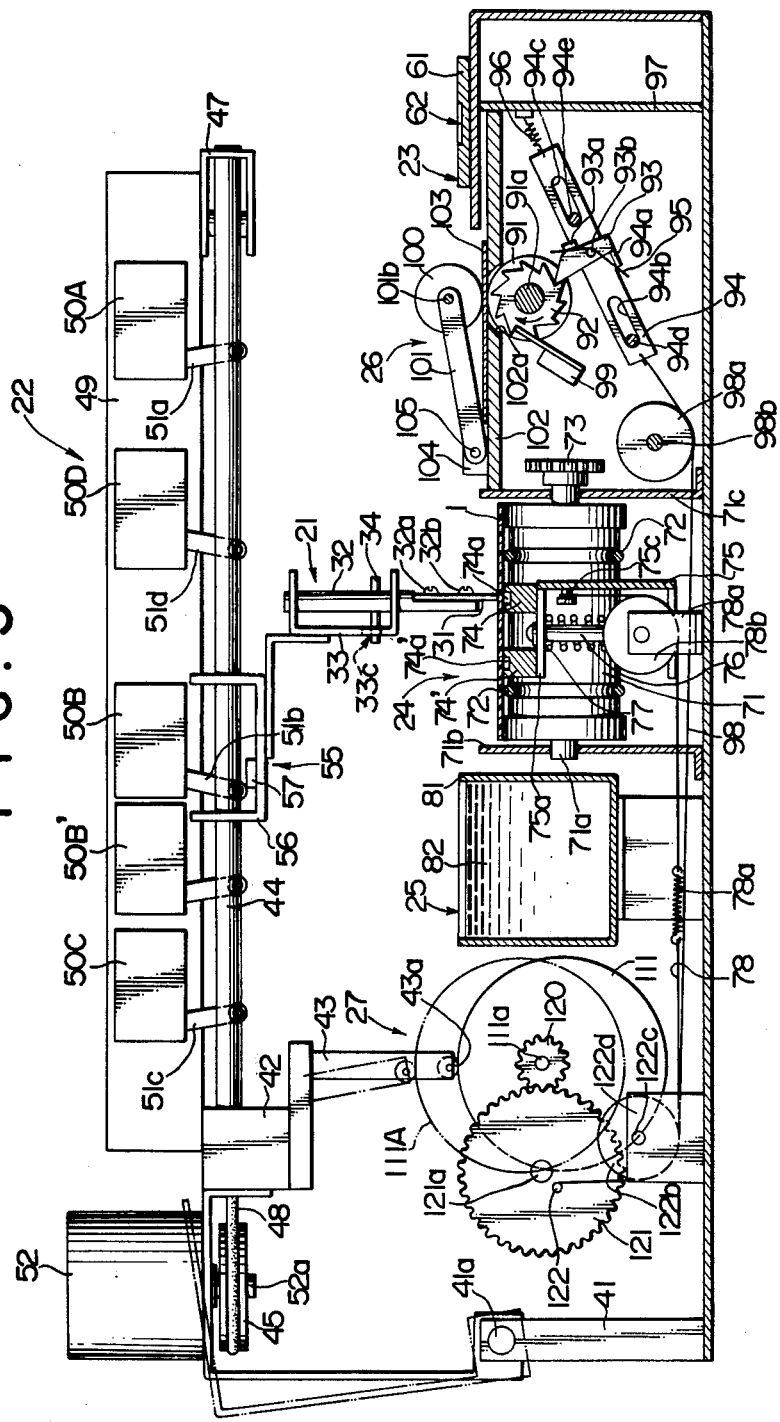
FIG. 5 is an elevational section of one form of a blood serum applicator.

Referring to FIG. 5, the serum applicator 5 includes a serum application member 21, a guide member 22 for moving the application member 21 in the horizontal direction, as viewed in this Figure, a serum dish assembly 23 disposed to apply a blood serum to the individual penpoints of the application member 21, an abutment 24 utilized when applying a serum to the film, a rinsing vessel 25 for cleaning the penpoints to remove any remaining serum, a drip device 26 for dripping the rinsing water from the penpoints, and a cam mechanism 27 for moving the guide member 22 in the vertical direction.

A side elevation of the application member 21, as viewed from one side of FIG. 5, is illustrated in FIG. 7. It comprises a plurality of penpoints 31 which are secured to stems 32 by means of set screws 32a, 32b, the stems being carried by a carrier 33. As will be noted from the cross section of FIG. 8, the carrier 33 is formed with pairs of aligned slot 33a, 33b, through which the stems 32 are inserted. A pin 34 secured to each stem 32 is inserted into a slot 33c formed in the base of the U-shaped carrier 33, thus preventing a free fall of the stem 32. As shown in FIGS. 9A and B, each penpoint secured to the lower end of the stem 32 comprises a pair of sheets, profiled as shown, secured together with a spacer 31c disposed therebetween (see FIG. 10). The amount of serum applied can be determined by suitably choosing the height D of a lower edge 31d which is formed along the frame portion at the free end of the penpoint structure.

Referring to FIG. 5, the guide member 22 has its lower end pivotally mounted on a stud 41a which is secured to a stanchion 41. A cross member 42 fixedly carries an arm 43 which in turn carries a roller 43a on its free end. Member 42 is also secured to a pair of parallel shafts 44. A motor 52 is mounted on one end of the guide member 22 and includes a shaft 52a on which a pulley 45 is mounted. Another pulley 46 is mounted on a cross member 47 which is secured to the shafts 44 at the other end thereof, and a rope 48 extends around the pair of pulleys 45, 46. A pair of longitudinal members 49 extend across the cross members 42, 47. A plurality of microswitches 50A, 50B ... are mounted on the longitudinal member at positions corresponding to the steps of serum supply, serum application and the like. These microswitches each have an actuator 51a, 51b ...

A carriage 55 is movable along the guide member for moving the serum application member 21 therealong. Referring to FIG. 11, the carriage comprises a channel-shaped body 56 which is formed with two pairs of holes 56a for passing the shafts 44, and also with a cutout 56b through which both runs of the rope 48 extend. One run of the rope 48 is secured to the carriage by suitable means as shown at 58. The carriage is formed with a transverse rib 57 which is operable to actuate the microswitches 50A, 50B ... As the motor 52 is set in motion, the pulley 45 rotates to drive the rope 48, whereby the carriage 55 moves along the shafts 44. When the carriage 55 moves to a position in which the rib 57 is aligned with the actuator 51b of the microswitch 50B, the rib actuates the switch to interrupt the rotation of the motor 52, as shown in FIG. 5. FIG. 12 shows the serum dish assembly 5c which receives a blood serum to be examined. The assembly 61 is formed with a plurality of recesses 61a, 61b, 61c ... for receiving the serum, the number of recesses being equal to the number of penpoints 31 on the application member 21 (see FIG. 7).

Figure 13:
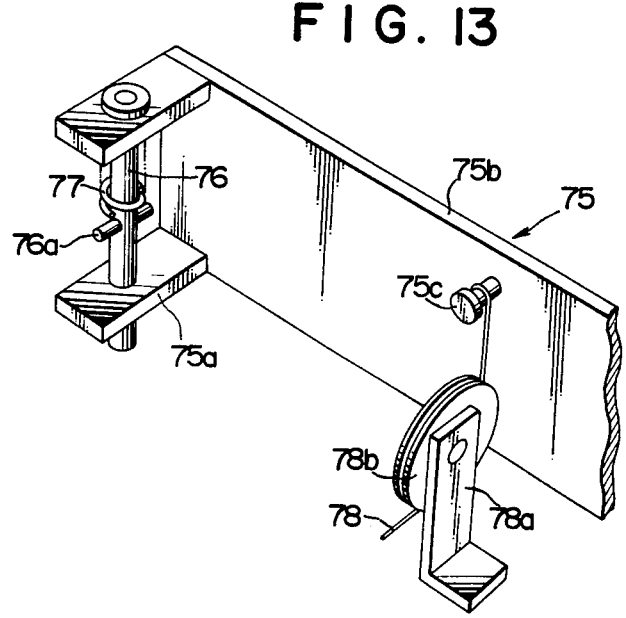
FIG. 13 is a perspective view of part of a holder framework for the serum applicator.

The abutment 24 utilized for the application of the serum will now be described. There is shown a roller 71 having a shaft 71a which is rotatably supported by a pair of oppositely located support plates 71b, 71c. While a single roller 71 is shown, there are a pair of such rollers disposed side by side and spaced by a distance which is slightly greater than the length of the application member 21. A plurality of belts 72 extend around the rollers 71. A gear 73 is coaxially connected with one of the rollers 71, and is driven for rotation by suitable drive means, not shown, for driving the rollers 71 and the conveyor belts 72 to feed the film 1 in a direction perpendicular to the plane of the drawing. A pair of abutment members 74, 74' extend in a direction perpendicular to the plane of the drawing their length being commensurate with the length of the application member 21. As shown, the abutment members 74, 74' are formed with elongate grooves 74a, 74'a centrally in their upper surface, and are supported by a holding stand 75 of the construction illustrated in FIG. 13. In FIG. 13, only one of the ends of the stand is shown, but its opposite ends 75a are channel-shaped and interconnected by a plate 75b. The abutment members 74, 74' are placed on and secured to the upper surface of the ends 75a which are slidably mounted on shafts 76 so as to be vertically movable therealong. A spring 77 is disposed on the shaft 76 between one end wall of the channel and a pin 76a is secured to the shaft 76 for normally urging the stand upward. A pin 75c is secured to a central portion of the plate 75b of the stand 75, and has one end of a wire 78 attached thereto. The wire 78 extends around a pulley 78b which is rotatably mounted on a bracket 78a, and extends to the left, as viewed in this Figure. As will be further described later, the wire 78 may be operated to move the stand 75 and hence the abutment members 74, 74' vertically up and down.

Figure 14:
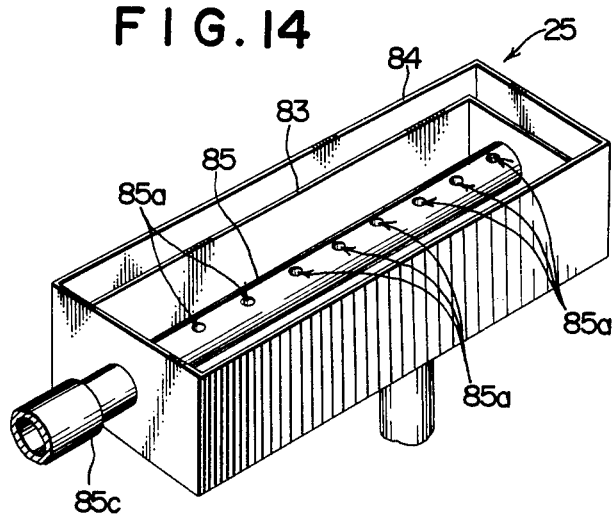
FIG. 14 is a perspective view of one form of rinsing unit.
Figure 15:
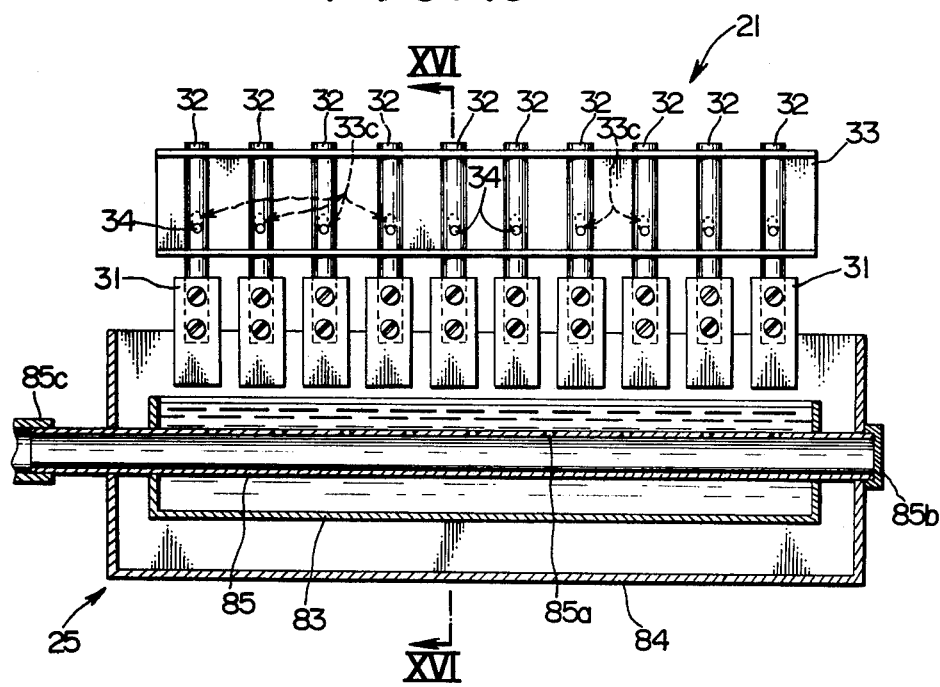
FIG. 15 is a cross section of the rinsing unit.
Figure 16:
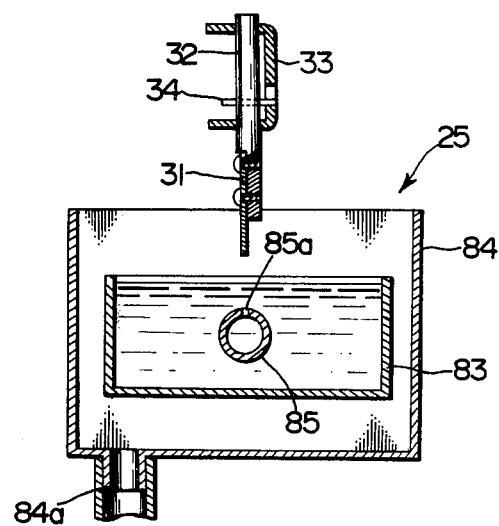
FIG. 16 is a cross section taken along the line XVI—XVI shown in FIG. 15.

The rinsing unit 25 comprises a vessel 81 containing a quantity of rinsing water 82, and in the embodiment shown, an arrangement is made to cause a flow of the water 82 in order to enhance the rinsing effect. By way of example, it may be constructed as shown in FIGS. 14 to 16. In these figures, there are shown a first vessel 83, a second vessel 84 having an outlet port 84a, and a piping 85 extending through both vessels and having a plurality of small apertures 85a formed in the top thereof. One end of the piping 85 is closed by a member 85b while the other end forms an inlet port 85c for receiving a rinsing water such as tap water. The rinsing water which is supplied through the port 85c jets through the apertures 85a to cause a flow thereof within the first vessel 83, thus assuring an efficient rinsing of the penpoints 31 which are placed into the vessel 83. An overflow of rinsing water from the vessel 83 is received by the vessel 84 to be discharged through the outlet port 84a.

Figure 17:
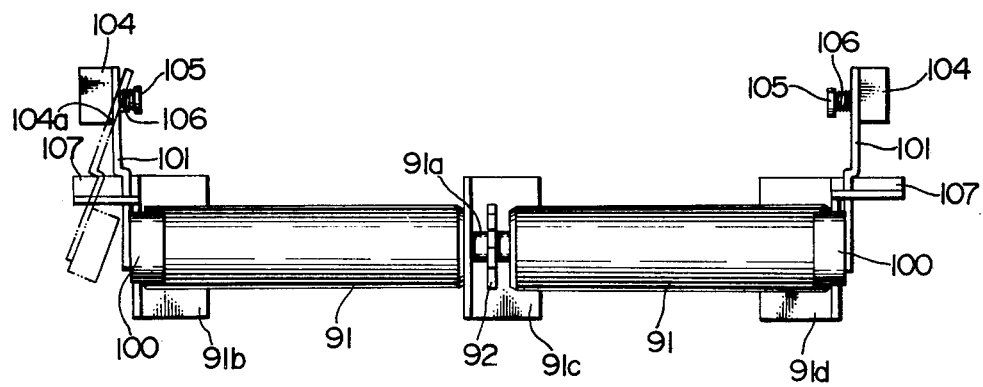
FIG. 17 is a plan view of a paper filter feed roller and its retaining roller.
Figure 18:
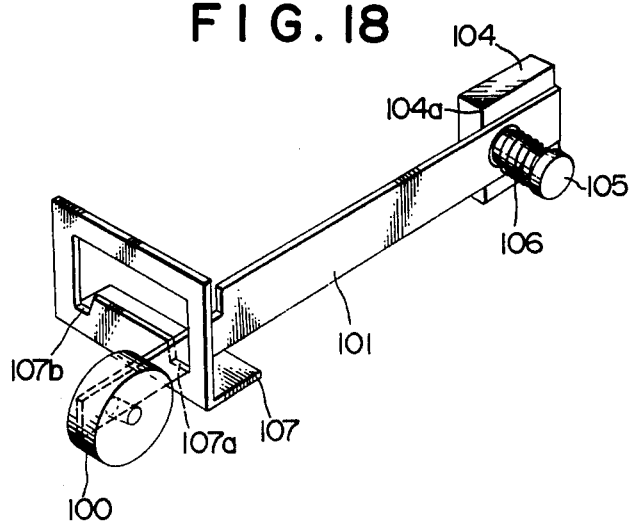
FIG. 18 is a perspective view of support means for the retaining roller.

FIG. 17 shows the drip device 26 comprised of a paper filter feed roller 91 which is formed in two parts as shown in FIG. 17, the roller has a shaft 91a which is supported by plates 91b, 91c, 91d shown in phantom line, and a ratchet wheel 92 is mounted thereon between the roller portions of the roller 91. A ratchet 93 cooperating with the ratchet wheel 92 has its shaft 93b rotatably mounted on a support member 94 and is urged to rotate clockwise by a spring 95 which engages a projection 93a on the ratchet and another projection 94a on the support member 94. The projection 94a on the support member 94 is effective to prevent a rotation of the ratchet 93. The support member 94 is formed with a pair of spaced elongate slots 94b, 94c, which are engaged by stationary pins 94d, 94e. A spring 96 has its one end secured to a mount 97 and its other end secured to the support member 94. A wire 98 is secured to the other end of the support member and extends around a pulley 98a which is rotatably mounted on a stationary shaft 98b. In this manner, the wire 98 may be utilized to effect a movement of the support member 94 and hence the ratchet 93 through a stroke defined by the slots 94b, 94c. By pulling the wire 98 to the left by means to be described later, the ratchet 93 may be moved to cause a rotation of the ratchet wheel 92 and hence the roller 91 through one tooth pitch. A detent 99 is associated with the ratchet wheel to prevent its rotation in the opposite direction. A retaining roller 100 is mounted on a shaft 101b which is supported by a bracket 101. The roller 91 slightly projects above the surface of a platform 102 through a notch 102a formed therein, and is engaged by the roller 100. When a paper filter 103 is placed on the platform 102 as shown in FIG. 5, the filter 103 is held between the rollers 91, 100. It is to be noted that the pair of rollers 100 located along the opposite ends of the roller 91 engage the opposite lateral edges of the filter 103. The brackets 101 each of which supports one of the rollers 100 are mounted to be pivotable by a construction to be described later, thereby permitting a vertical movement of the rollers 100 and facilitating the placement of the paper filter 103 on the platform 102. Referring to FIGS. 17 and 18, the other end of the bracket 101 is mounted on a support 104 using a pin 105 in a manner such that it is rotatable around the pin 105 and is displaceable lengthwise of the pin, but its movement is normally prevented by a spring 106. A guide frame 107 is disposed adjacent to the retaining roller 100, and can be utilized to manually move the bracket 101 from a recess 107a therein to another recess 107b. When the bracket is moved from the position shown in broken lines in FIG. 17, the bracket 101 angularly moves around one corner 104a of the support 104 such that its portion nearer the roller 100 moves to the left while the other side moves to the right against the resilience of the spring 106, as viewed in FIG. 18. Conversely, as the bracket 101 is manually raised when it is located in the recess 107b in the guide frame 107, the resilience of the spring 106 causes the roller carrying portion of the bracket to move into the recess 107a.

Figure 19:
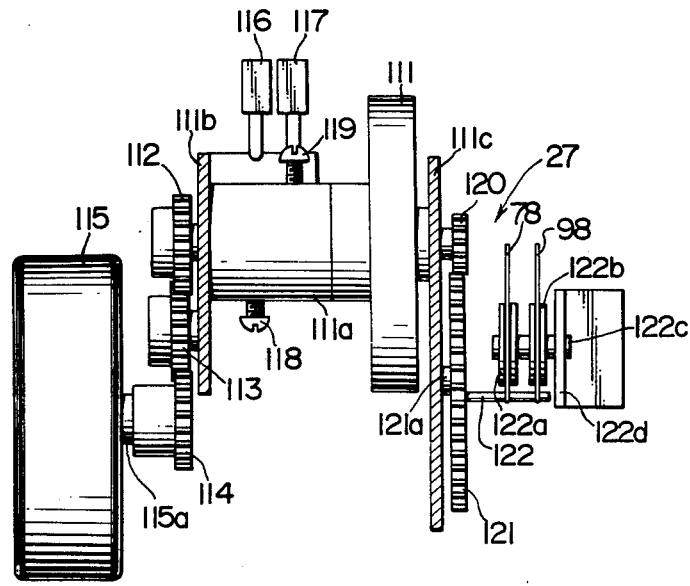
FIG. 19 is a plan view of a cam mechanism for the applicator.

Referring to FIG. 19, the cam mechanism 27 will be described. It includes an eccentric cam 111 having a rotatable shaft 111a on which a gear 112 is fixedly mounted. The shaft 111a is supported by a pair of support plates 111b, 111c, and the gear 112 is connected through other gears 113, 114 with the rotary shaft 115a of a motor 115. Thus, the eccentric cam 111 rotates when the motor 115 is set in motion. A pair of microswitches 116, 117 are provided adjacent to the shaft 111a, and are operated by a pair of pins 118, 119 which are fixedly mounted on the shaft 111a. When actuated, the microswitch 116 is effective to interrupt the rotation of the motor 115 and to set the motor 52 (see FIGS. 5 and 6) in motion which acts to move the carriage 55 (see FIG. 11). The microswitch 117 is disposed so as to be actuated at an angular spacing of 180° exactly around the periphery of the eccentric cam 111 from the position in which the microswitch 116 is actuated, thereby deenergizing the motor 115 to maintain the serum application member 21 in its lower position in order to rinse any serum off the penpoints of the application member within the rinsing vessel, for example. There is provided a timer which re-initiates the energization of the motor a given time interval after the interruption of the energization thereof by the switch 117.

A gear 120 is fixedly mounted on one end of the shaft 111a and meshes with a reduction gear 121 mounted on a shaft 121a, these gears having a gear ratio of 1:4. A pin 122 is mounted on the face of the reduction gear 121 at an eccentric position, namely, remote from the shaft thereof, and is connected with the end of wires 78, 98 which extend around coaxial pulleys 122a, 122b of an equal diameter mounted on a shaft 122c which is supported by a support plate 122d. Thus, as the eccentric cam 111 rotates, the transmission through the gears 120, 121 causes the pin 122 to rotate about the shaft 121a of the reduction gear 121, thereby moving the abutment member 74 vertically up and down and rotating the paper filter feed roller 91 for the drip device 26. It will be noted that a buffer spring 78a is connected in the wire 78.

The operation of the overall applicator will be described with reference to the timing diagram of FIG. 20 which shows the interrelationship of operations of the motors and microswitches. The operation starts with locating the penpoints 31 of the application member 21 above the serum dish assembly 61. A specimen or serum to be examined is supplied to the number of recesses 61a, 61b . . . in the assembly 61, which is disposed at a position shown in FIG. 5. The motor 115 is then set in motion at time $t_0$ shown in FIG. 20. This causes a rotation of the gear 112 through the gears 113, 114, rotating the eccentric cam 111. As the eccentric cam 111 rotates, it moves from a position 111A shown in phantom line in FIG. 5 toward a solid line position progressively, causing a downward movement of the arm 43 carrying the roller 43a which bears against the cam surface. As a result, the guide member 22 also moves downward, and when the eccentric cam 111 has reached the solid line position of FIG. 5, the penpoints 31 of the application member 21 will be immersed into the serum received in the recesses 61a, 61b . . . , whereby the serum is applied to the respective penpoints. As the eccentric cam 111 further rotates, the arm 43 begins to move upwardly and reaches an uppermost position shown in phantom line at time $t_1$. The pin 118 on the shaft 111a then actuates the microswitch 116, which interrupts the energization of the motor 115 to stop the rotation of the cam 111. Simultaneously, the motor 52 is set in motion, whereby the rope 48 moves, moving the carriage 55. Consequently, the application member 21 secured to the carriage 55 moves to the left, as viewed in FIG. 5. When the carriage 55 reaches the position of the microswitch 50B, the rib 57 thereof pushes up the actuator 51b of the microswitch 50B, thus actuating the latter. Though the carriage 55 moves past the position of the microswitch 50D before it reaches the microswitch 50B, the microswitch 50D is disposed to be actuated only during the movement of the carriage to the right, and therefore is not actuated during the described movement of the carriage to the left. As shown at time $t_2$ in FIG. 20, the motor 52 ceases to rotate while the motor 115 is again set in motion. This causes a downward movement of the guide member 22 and hence the serum application member 21. As the application member 21 moves downward, the pin 122 on the reduction gear 121 moves in a direction tending to reduce the tension in the wire 78, and the tension of the wire 78 will be at its minimum value when the pin 122 reaches the position shown in FIG. 5. Thus, the spring 77 becomes effective to raise the stand 75. During the time such operation takes place, the serum bearing film 1 wetted with the buffer solution and which has been fed by the rollers 11, 12 is fed on the belts 72 in a direction perpendicular to the plane of FIG. 5, by the rotation of the roller 71 of the abutment 24 until it reaches a given position on the belts where it comes to a stop. As a consequence, when the application member 21 moves down in the manner mentioned above, the penpoints 31 mounted thereon gently press against the surface of the film 1 placed on the belts 72 while the abutment member 74 support the film 1 from below, thus assuring a satisfactory application of the serum to the film. The presence of grooves 74a in the abutment member 74 provides a space below the film 1 where the serum is to be applied, thus facilitating the application of the serum to the film 1. As the eccentric cam 111 further rotates, the arm 43 moves upward, accompanying an upward movement of the guide member 22 and the application member 21. As the eccentric cam 111 continues to rotate, the reduction gear 121 also rotates, whereby the pin 122 thereon pulls the wire 78 to cause a downward movement of the stand 75 and the abutment member 74. When the abutment member 74 completely moves away from the lower surface of the film 1, a drive is applied to the roller 71 to convey the belts 72, feeding the film 1 to which the serum is applied, to the next step.

Figure 20:
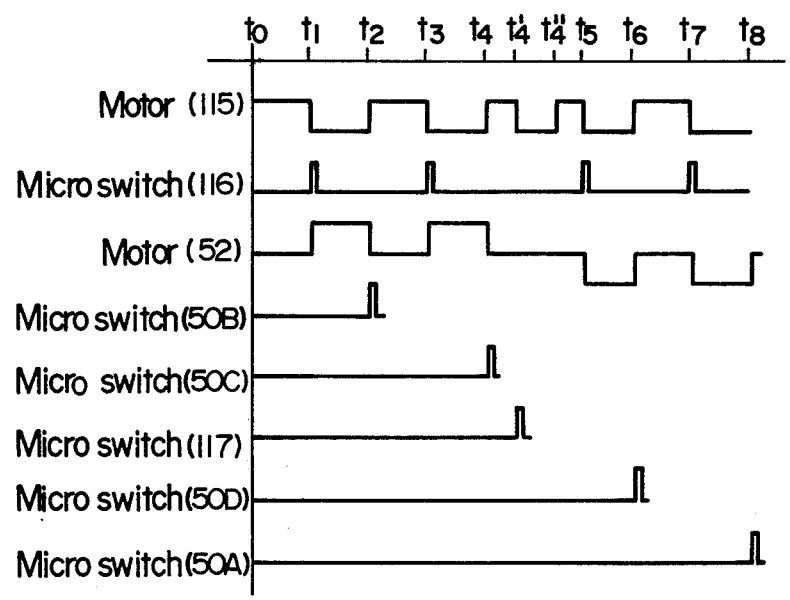
FIG. 20 is a timing chart illustrating the relationship of the operation of various parts of the serum applicator.

At time t₃ shown in FIG. 20 when the guide member 22 reaches its uppermost position, the microswitch 116 operates to interrupt the rotation of the motor 115 while the motor 52 is again set in motion to move the carriage 55 to the left along the guide member 22. When the carriage 55 reaches the position of the microswitch 50C, which corresponds to time t₄ of FIG. 20, the microswitch 50C operates to interrupt the rotation of the motor 52 while the rotor 115 is set in motion, causing a downward movement of the guide member 22. During the movement of the carriage 55 from the position of the microswitch 50B to that of 50C, it moves past the microswitch 50B', which however remains ineffective at this time since it is operated only when it becomes necessary to change the position at which the application of the serum to the penpoints takes place, from one of the abutment members, 74, to the other 74' for the reason to be described later. If the position at which the application of the serum takes place is changed to the abutment member 74' and the microswitch 50B becomes effective, the microswitch 50B is rendered inoperative. In this manner, the carriage 55 comes to a stop at the position of the microswitch 50C, and as the application member 21 moves down, the penpoints 31 of the application member 21 are immersed into a rinsing water 82 contained in the rinsing vessel 81. At this time (t'₄ of FIG. 20), the microswitch 117 is actuated to deenergize the motor 115, whereby the penpoints 31 are held immersed in the rinsing water 82 for a time interval which is required to remove any serum attaching to the penpoints 31 completely. At time t''₄, the timer times out to set the motor 115 in motion again, thereby moving the guide member 22 upward.

At time t₅ of FIG. 20, the microswitch 116 is actuated to interrupt the rotation of the motor 115 while the motor 52 is set in motion in the reverse direction to move the carriage 55 in the opposite direction or to the right. For the reason mentioned above, the microswitch 50B remains ineffective, so that when the carriage 55 reaches the position of the microswitch 50D at time t₆, the motor 52 is deenergized while the motor 115 is set in motion, repeating a similar operation. The downward movement of the guide member 22 brings the penpoints 31 of the application member 21 into abutment against the paper filter 103, removing any rinsing water which remains attached thereto. When the application member 21 moves upward after the rinsing water is wiped off from the penpoints 31, the microswitch 116 is actuated at time t₇ to interrupt the operation of the motor 115 while the motor 52 is set in motion in the opposite direction, whereby the carriage 55 moves to the right. When it reaches the position of the microswitch 50A, the latter is actuated to stop the movement of the carriage at time t₇. This completes one cycle of operation of the serum applicator 5.

During the cycle just described, the eccentric cam 111 rotates through four revolutions while the reduction gear 121 rotates through one revolution. As mentioned previously, the pin 122 is located on the reduction gear 121 such that the tension in the wire 78 will be minimized when the application of the serum to the film 21 takes place by means of the application member 21 as shown in FIG. 5, and thus the abutment member 74 assumes its uppermost position at this time. On the other hand, the other wire 98 is pulled only once during one cycle of operation of the applicator, moving the support plate 94 to enable the ratchet 93 to permit a rotation of the ratchet wheel 92 through one tooth pitch. This accompanies a rotation of the roller 91, which feeds a given length of the paper filter 103. Thus, the portion of the paper filter 103 which is wetted by wiping the penpoints subsequent to the rinsing step will be fed away, by the time the penpoints will move down onto the paper filter the next time, and a fresh portion of the paper filter will be presented for the next wiping or drip step. A simple abutment of the penpoints 31 against the paper filter 103, between the downward and upward movements of the application member 21, is insufficient for the purpose of dripping, and therefore it is desirable that the penpoints 31 be maintained in abutment against the paper filter 103 for a given time interval. This assures a complete removal of any rinsing water attaching to the penpoints. To this end, an arrangement may be made so that the microswitch 117 becomes effective during the drip step so that the rotation of the motor 115 is interrupted when the application member 21 has moved down and is re-initiated by a timer, not shown, after a given time interval.

Figure 21:
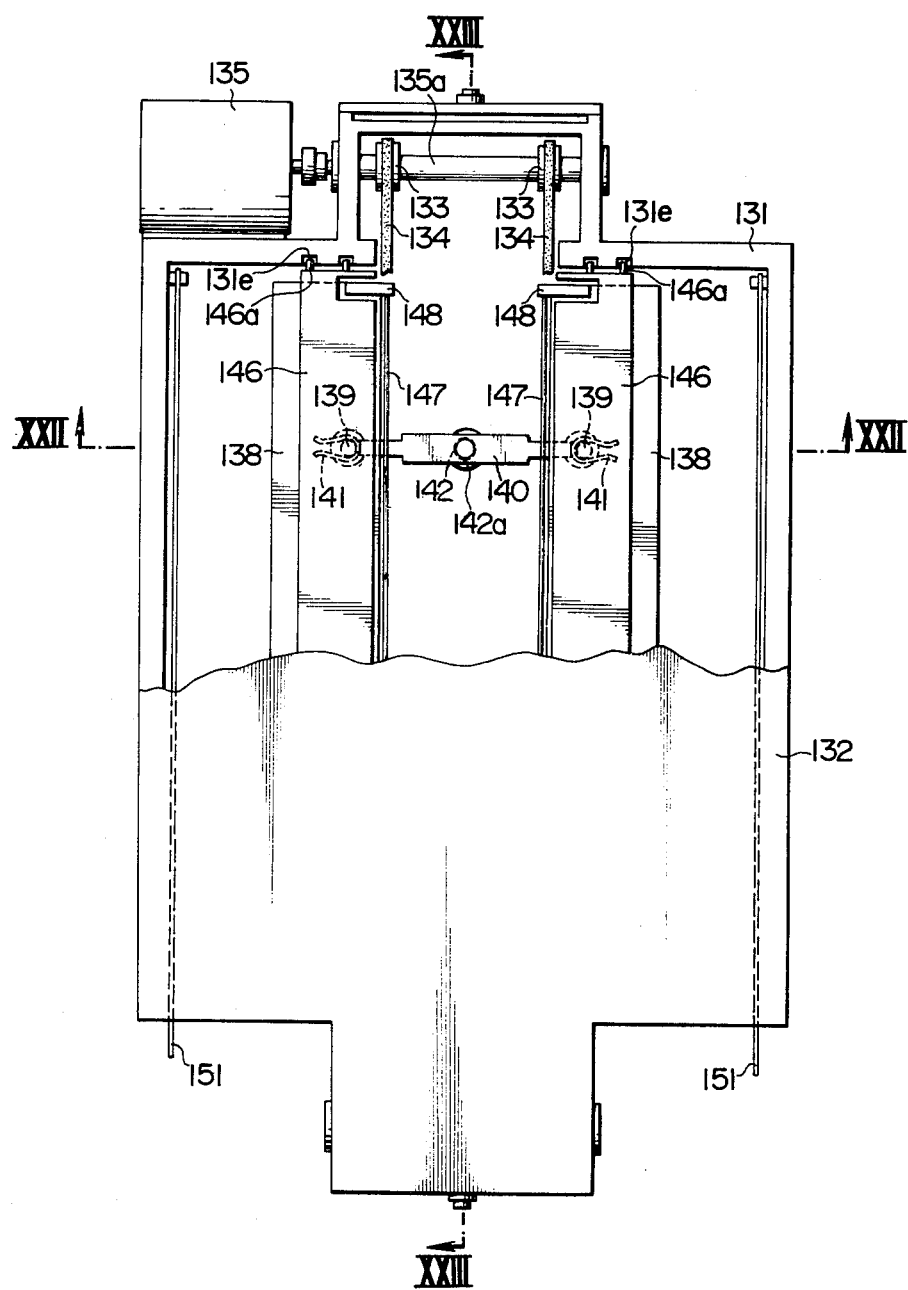
FIG. 21 is a plan view, partly broken away, of a cataphoretic compartment.

FIG. 21 shows the cataphoresis compartment 6 in plan view, with a portion being broken away. The compartment includes a body 131 which is closed by a lid 132 and in which a pair of rollers 133 are housed adjacent to a film inlet 131a and a film outlet 131b, respectively (see FIG. 23). Endless belts 134 extend around the pairs of rollers 133 for conveying the film. A motor 135 is located outside the body 131 and has its output shaft 135a extending into the body 131 in which one pair of rollers 133 are mounted thereon. The rotation of the motor 135 causes the rollers 133 to rotate, thus driving the endless belts 134. When the film is inserted through the inlet 131a, it is conveyed on the belts 134 through the body 131. Subsequent to the cataphoretic process carried out in the body 131, the belts 134 may be driven again to convey the film out of the body 131 through the outlet 131b.

Figure 22:
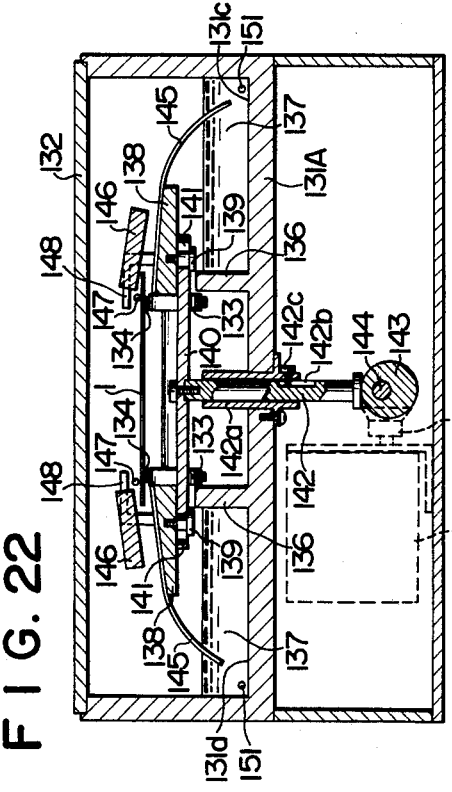
FIG. 22 is a cross section taken along the line XXII—XXII shown in FIG. 21.
Figure 23:
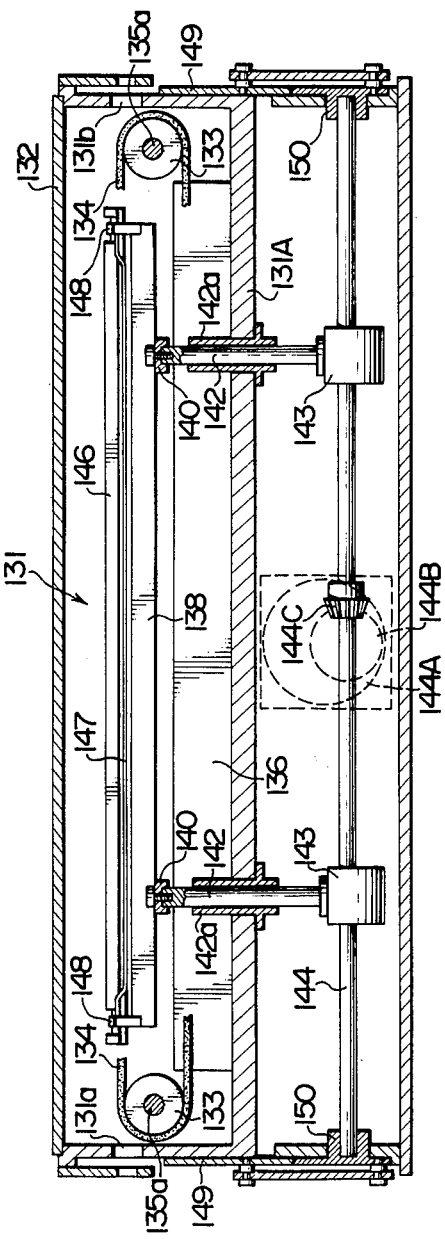
FIG. 23 is a cross section taken along the line XXIII—XXIII shown in FIG. 21.

As shown in FIG. 22, a pair of partitions 136 are integrally formed with the body 131 to define a pair of vessel-like chambers 131c, 131d, both of which contain a quantity of buffer solution 137. A pair of receivers 138 are disposed symmetrically on opposite sides of the longitudinal center line of the body 131 and each has a tapered upper surface, as will be noted from FIG. 22. A pair of support arms 140 are axially spaced apart and each has a pair of springs 141 secured to its opposite ends, which hold screws 139 secured to the receiver 138, thus detachably supporting the receivers 138. A pair of posts 142 slidably extend through hollow shafts 142a secured to and extending through a shelf 131A of the body 131, and are vertically movable as a result of the engagement of their axial guide grooves 142b and stationary pins 142c. The posts 142 each serve as the means for supporting the support arms 140. A pair of cams 143 are disposed in alignment with the posts and are mounted on a shaft 144 which is disposed in the lower part of the body 131 so as to extend longitudinally thereof in a rotatable manner. It will be noted that the rotation of the cams 143 permits a vertical movement of the posts 142 and hence the receivers 138. A paper filter 145 has its one end placed on the top face of each receiver 138 and its other end dipped in the buffer solution 137. A pair of strip-like retainers 146 are disposed over the receivers 138 and are maintained at a given level as shown, by inserting pins 146a secured thereto into grooves 131e formed in the body 131. A pair of wires 147 extend substantially over the belts 134 and have their ends fixed to fixtures 148 which are secured to the receivers 138. As shown in FIG. 23, the inlet 131a and the outlet 131b can be closed by vertically slidable coverplates 149, which can be moved up and down by a crank mechanism 150. Numeral 151 represents electrodes.

In operation, the film 1 to which the serum has been applied is conveyed on the belts 72 into the inlet 131a of the body 131. Simultaneously, the motor 135 is set in motion to drive the endless belts 134, whereby the film 1 is conveyed on the belts 134 into the body 131. When the film 1 reaches a given position, the drive of the belts 134 is interrupted and the shaft 144 is rotated by a suitable drive mechanism such as a motor 144A and bevel gears 144B, 144C, which are located adjacent to the shaft 144 in the lower portion of the body 131. Thereupon, the cams 143 undergo rotation to push up the receivers 138 into abutment against the lower surface of the retainers 146. As shown in FIG. 22, the spacing between both belts is chosen less than the width of the film 1, so that both lateral edges of the film 1 project beyond the belts 134. Thus, as the receivers 138 are raised, the film 1 is moved away from the belts and is held sandwiched between the receivers 138 and the retainers 146 together with the paper filters 145. By applying a voltage across the electrodes 151 under this condition, the film 1 is electrically energized through the paper filters 145 having their one end dipped into the buffer solution 137.

When the shaft 144 rotates, the crank mechanisms 150 also raises the coverplates 149, so that the inlet 131a and the outlet 131b are both closed at the same time as the receivers 138 are raised by the rotation of the cams 143. In this manner, the energization takes place in a closed compartment, permitting a cataphoretic process. After the energization is maintained for a given time interval, the shaft 144 is rotated again to lower the receivers 138 and the coverplates 149. As the receivers 138 move down, the wires 147 extending across the fixtures 148 secured thereto also move down, reliably releasing the film 1 from the retainers 146 if the film happens to be adhering thereto.

Subsequent to the cataphoretic process, the film is placed on the belts 134, and energizing the motor 135 again, the belts 134 are driven again to convey the film 1 to the next step through the outlet 131b.

When the cataphoresis compartment is operated for a prolonged period of time for the energization of a number of films, an adverse influence upon the measuring results may be caused in the fractionated patterns because of a varying ion concentration of the buffer solution in the compartment in which the electrodes are disposed. This difficulty can be overcome by changing the polarity of the electrodes from time to time. By way of example, the polarity of the electrodes may be reversed for the energization of each film. However, when the polarity is changed, it is also necessary to change the position at which the serum is applied to the film. The microswitch 50B' is provided at this end to stop the carriage 55 at the position where it is disposed, so that the penpoints 31 of the application member 21 is lowered to the position of the abutment member 74', thus changing the position on the film 1 at which the serum is applied. The switching between the microswitches 50B and 50B' to change the serum application position on the film, combined with the change of the polarity of the electrodes in the cataphoresis compartment assures the achievement of satisfactory fractionated patterns over a prolonged period of use.

Alternatively, a pair of cataphoresis compartments may be juxtaposed and made transversely movable so as to permit their alternate use. Thus the cataphoretic process can be efficiently conducted conveying a film into one of the compartments while the other compartment is energized.

Figure 24:
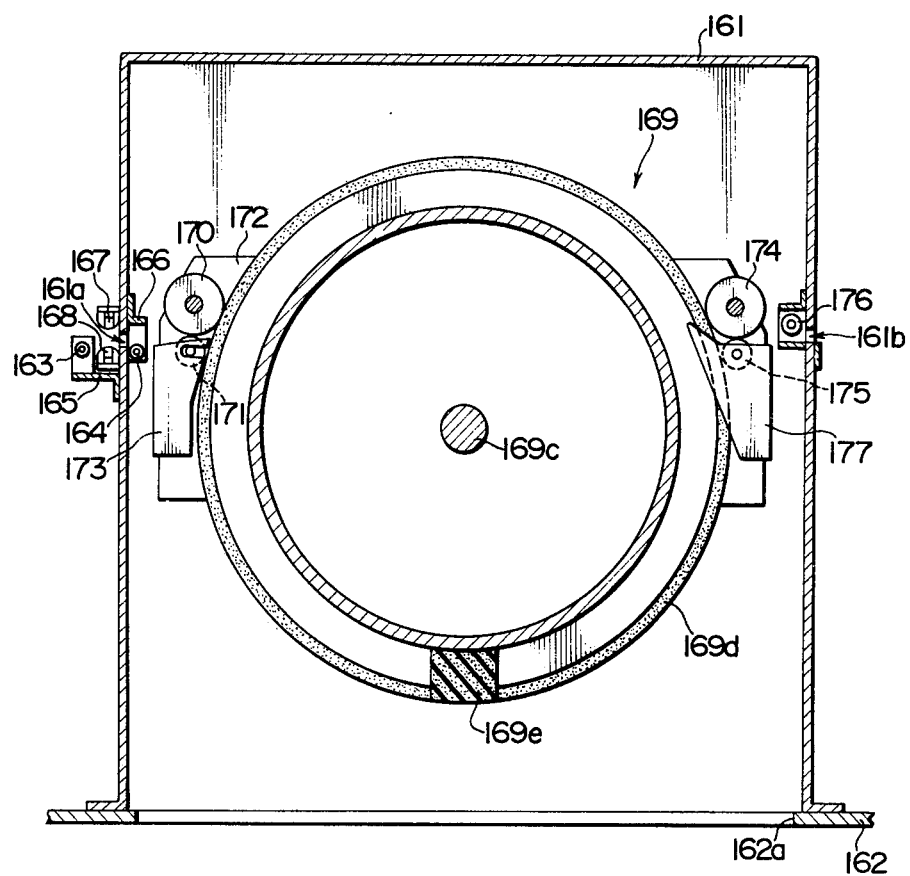
Figure 25:
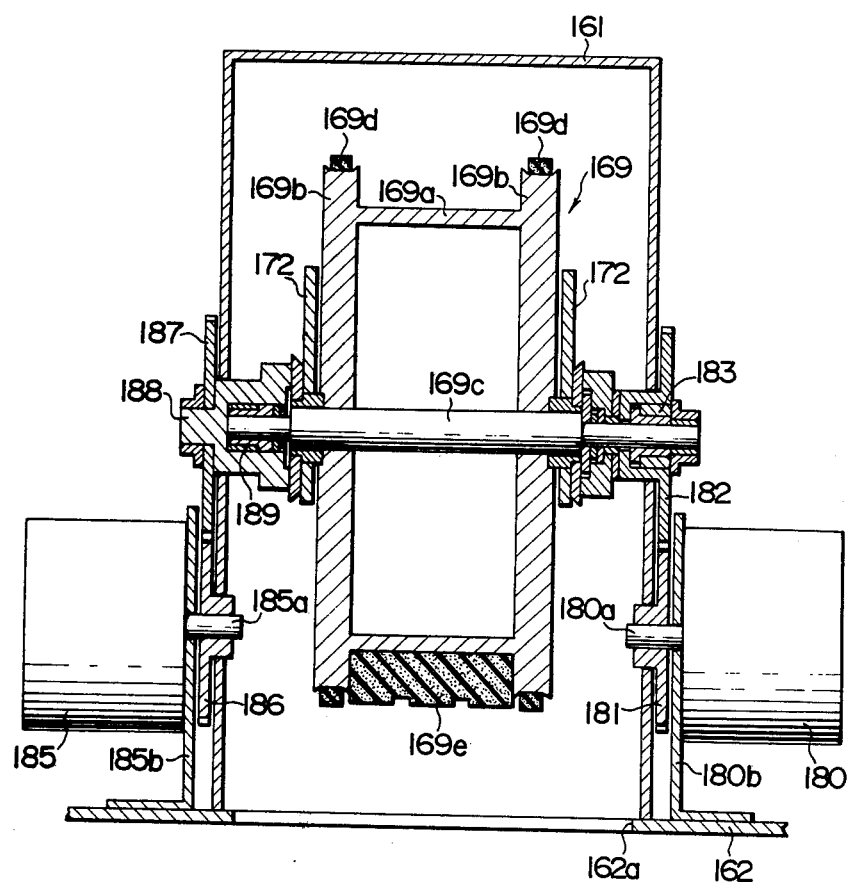
Figure 26:
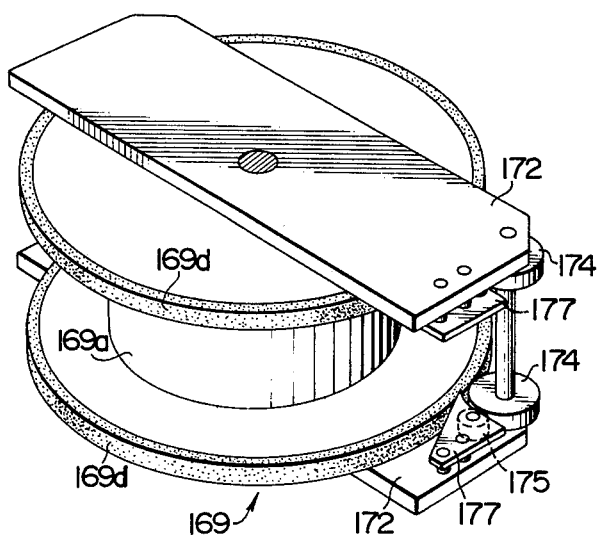
FIG. 26 is a view in perspective, of dyeing, decolorizing and drying stations.

Referring to FIGS. 24 and 25, there is shown the dyeing, decolorizing and drying station 7. As shown, it includes a casing 161 placed on a base plate 162. The casing 161 includes an inlet 161a, adjacent to which a pair of rollers 163, 164 are mounted on brackets 165, 166. A light emitting diode 167 and a light receiving element 168 are disposed above and below the inlet 161a to detect the movement of the film therethrough. A drum 169 is rotatably mounted within the casing 161 by means to be described later, and has a recess 169a peripherally, together with opposite sides 169b, as will be noted from FIGS. 25 and 26. Film attaching members 169d, 169e which comprise a material such as sponge are secured to part of the opposite sides 169b and the recess 169a of the drum 169, respectively. A pair of rollers 170, 171 are mounted on a bracket 172. The roller 170 is spring biased (not shown) in a direction toward the center of the drum 169 and is maintained in engagement therewith. A film guide member 173 is mounted on the bracket 172. In a similar manner, there are provided rollers 174, 175, 176 and a film guide member 177 adjacent to the outlet 161b. Referring to FIG. 25, a mechanism for rotating the drum 169 will be described. A first motor 180 is mounted on a support plate 180b and has an output shaft 180a on which an output gear 181 is mounted and meshes with a drive gear 182. A one way clutch 183 is adapted to transmit the rotation of the gear 182 to the shaft 169c of the drum only when it rotates clockwise, as viewed from the right-hand side of FIG. 25. A second motor 185 is mounted on a support plate 185b and has an output shaft 185a on which an output gear 186 is mounted and meshes with another gear 187. The gear 187 is fixedly mounted on a shaft 188, one end of which is secured to the bracket 172. A one-way clutch 189 is adapted to transmit the rotation of the shaft 188 to the drum shaft 169c only when it rotates counter-clockwise, as viewed from the left-hand side of FIG. 25.

Figure 28:
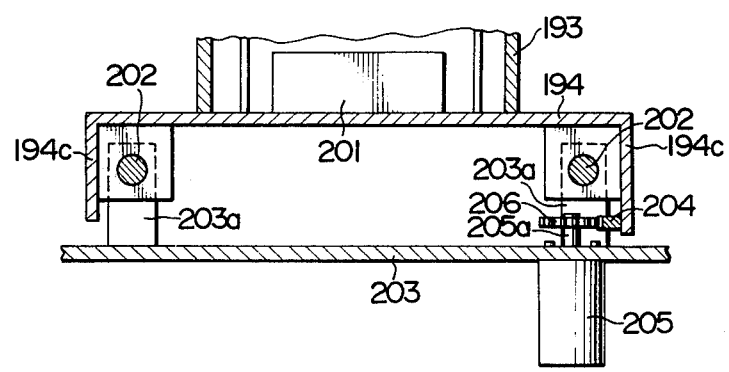

FIG. 27 shows a vessel for dyeing solution, a vessel for decolorizing solution and a drying unit. These units are located below the base plate 162 on which the casing 161 is mounted. In FIG. 27, it will be noted that a dyeing solution vessel 191, a decolorizing solution vessel 192 and a drying unit 193 are supported by a framework 194. The vessel 191 contains a dyeing solution 195 which comprises a solution of Ponceau 3R dissolved in acetic acid trichloride. The vessel 192 contains a decoloring solution 196 which comprises a diluted solution of acetic acid, which may be poured through an inlet 197. The bottom of the vessel 192 is provided with a conduit 198 for discharging the decolorizing solution 196, and the conduit 198 may be either closed or opened by the action of the solenoid valve 199. Openings 194a, 194b are formed in the framework 194 below the vessels 191 and 192, respectively, for purposes to be described later. The drying unit 193 comprises a heater 200 and a fan 201, so that a heated dry air can be blown upward through ventilation openings 193a. A shaft 202 is attached to a mount 203 by means of support members 203a, and supports the framework 194 so as to be movable in the horizontal direction, as viewed in FIG. 27. A rack 204 is mounted on a plate portion 194c extending downward from the framework 194 as shown in FIG. 28, and a motor 205 is fixedly mounted on the lower surface of the mount 203. A pinion 206 is fixedly mounted on the rotary shaft 205a of the motor 205 and meshes with the rack 204. A lead screw 207 threadably engages a nut 208 disposed on the mount 203 for vertical movement, and is located directly below the opening 194a in the position of FIG. 27. A gear 209 is integral with the nut 208, and meshes with a gear 211 which is fixedly mounted on the output shaft 210a of a motor 210 which is in turn fixedly mounted on the underside of the mount 203. The rotation of the motor 210 causes the nut 208 to rotate, thereby moving the lead screw 207 vertically. A movement control plate 212 is fixedly mounted on the lead screw 207 and is integrally movable in the vertical direction together with the lead screw 207 while being guided by a guide rod 216. A pair of limit switches 213, 214 are secured to a bracket 215 which is fixedly mounted on the mount 203, and are adapted to be operated by the free end of the control plate 215 for controlling the energization of the motor 210 and hence the vertical movement of the lead screw 207.

In operation, the film which has been subjected to the cataphoretic process in the cataphoresis compartment to form fractionated patterns is fed into the inlet 161a of the casing 161. The presence of the film at the inlet is detected by the combination of the diode 167 and the element 168, which acts to set the drum 169 in motion, by energizing the first motor 180. This causes the gear 182 to rotate clockwise, as viewed from the right-hand side of FIG. 25, and the rotation of the gear 182 is transmitted to the shaft 169c, so that the film which has been fed to the drum surface is now fed while being carried around the periphery of the drum 169 in a sticking manner, and is eventually carried by the member 169d of a material such as sponge. More specifically, when the leading end of the film reaches the drum surface, it attaches to the attaching member 169e, which is so located by adjusting the starting position of the drum 169. Subsequently, it attaches to successive attaching members 169d which are secured to the opposite sides of the drum 169 while it is being fed. By choosing the length along the drum surface measured from the roller 170 to the roller 174 to be slightly less than the film length, the rotation of the drum 169 is interrupted when the leading end of the film is located between the drum 169 and the drum 174. The film then remains attached to the drum 169 since its opposite ends are held sandwiched between the rollers 170, 174 and the drum 169. The first motor 180 is deenergized at this time while simultaneously energizing the second motor 185. When the motor 185 is set in motion, the gear 187 rotates counter-clockwise, as viewed from the lefthand side of FIG. 25, and the rotation of this gear is transmitted through the shaft 188 and one-way clutch 189 to the shaft 169c of the drum 169. Thus the retainer 172 secured to the shaft 188 rotates integrally with the drum 169. As a consequence, the entire assembly rotates while the film is held between the rollers 170, 174 and the drum 169. When the drum 169 has rotated through one-half revolution exactly to place the film in its lowermost position around the periphery thereof, the motor 185 is deenergized. Then the relative position of the rollers 170, 174 and the drum 169 will be exactly opposite from the position shown. The motor 210 shown in FIG. 27 is then set in motion to rotate the nut 208 through the gears 211, 209, thereby causing the lead screw 207 to move upwardly into the opening 194a. The upward movement of the lead screw 207 is effective to raise the vessel 191, which is therefore driven upwardly through the opening 162a in the base plate 162 into the casing 161 to a level in which the lower portion of the drum 169 is immersed in the dyeing solution 195. In this manner, the film is also immersed into the dyeing solution. When the lead screw 207 has moved far enough upwardly to permit a perfect immersion of the film in the dyeing solution, the control plate 212 actuates the limit switch 213, which then deenergizes the motor 210 to stop the upward movement of the lead screw 207. After the film is held immersed in the dyeing solution for a given period of time required to complete the dyeing step, the lead screw 207 is moved down to lower the vessel 191. When it reaches the position shown in FIG. 27, the control plate 212 actuates the other limit switch 214, which operates to stop the downward movement of the lead screw. Then the motor 205 is energized to rotate the pinion 206, which cooperates with the rack 204 to move the framework 194 to the left, as viewed in FIG. 27. This movement is interrupted when the opening 194b formed in the framework at a position below the vessel 192 is aligned with the lead screw 207. Now, the lead screw 207 is operated again to raise vessel 192 until the film can be immersed in the decolorizing solution 196 contained therein in a similar manner to that described for the dyeing vessel 191. After a given time interval, the valve 199 is opened, discharging the contaminated decolorizing solution through the drain conduit 198. When the solution is completely discharged, the valve 199 is closed and a fresh supply of decolorizing solution is supplied through the inlet 197 to repeat a decolorizing operation. Upon completion of the decolorizing step, the lead screw 207 is moved downward to lower the vessel 192 and is stopped at the position corresponding to the limit switch 214. Finally, the framework 194 is further driven to the left until the drying unit 193 is aligned with the opening 162a, whereupon heated air is supplied therefrom to dry the film.

Subsequently, the second motor 185 is set in motion to return the drum 169, retainer 172 and rollers 170, 174 to their original position, whereupon the motor 185 is deenergized while the first motor 180 is set in motion to rotate the drum, thus feeding the film. As shown by the perspective view of FIG. 26, the tip of the guide member 177 projects slightly into the space of the drum 169, and this serves to aid in separating the film from the drum surface, thus passing it between the rollers 174, 175 and the guide member 177 and through the outlet 161b of the casing 161 to the next following colorimetric determination step.

While in the above description, the film has been held attached to the drum 169 during its rotation together with the retainer 172 and the rollers 170, 174 and held stationary in its lowermost position while the dyeing and decolorizing vessels are raised, it should be understood that the drum 169 may be maintained in continuous rotation together with other members while holding the film attached thereto when the vessels 191, 192 are moved up and down. In this instance, the film is interruptedly and repeatedly subjected to the dyeing and decolorizing steps since the drum rotates continuously. This approach minimizes the necessary supply of the dyeing and decolorizing solutions and achieves a uniform dyeing and decolorizing ffect as a result of the film passing through the solutions.

Figure 29:
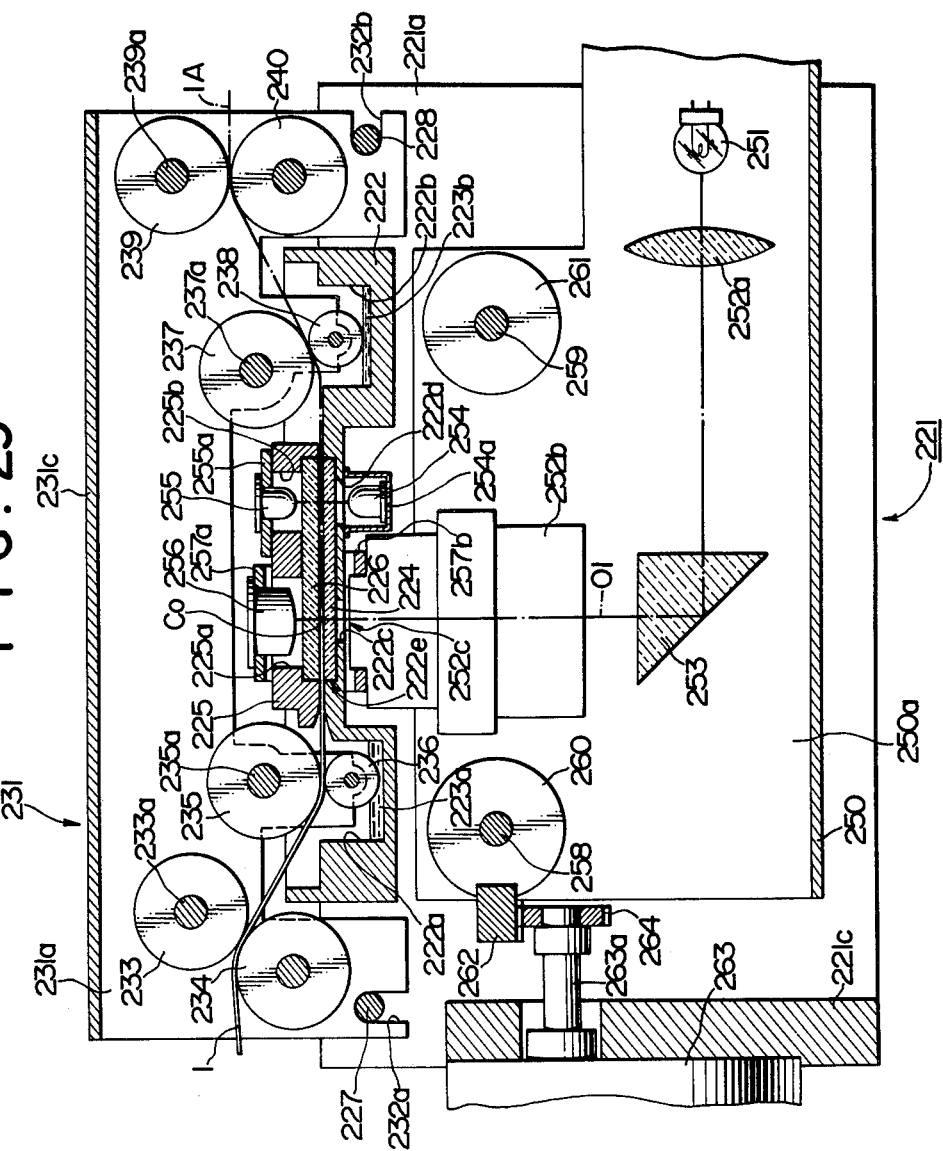
FIGS. 29 to 32 are views showing the construction of one form of a densitometer.
Figure 30:
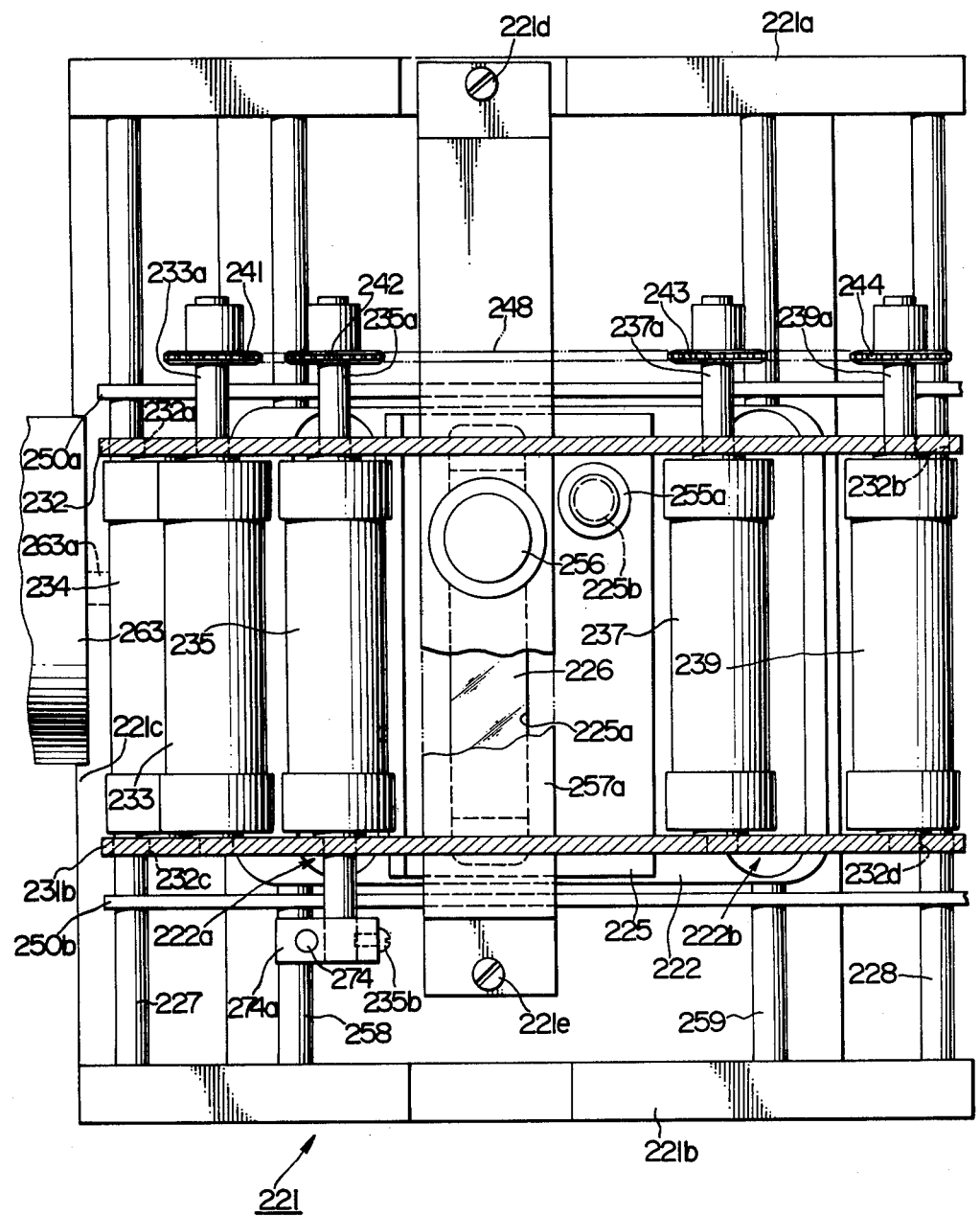

The densitometer 8 will now be described. Referring to FIGS. 29 and 30, an apparatus 221 for quantitative analysis comprises a pair of sideplates 221a, 221b which are firmly connected together by a pair of interconnecting rods 227, 228 and a pair of guide rods 258, 259. A liquid vessel 222 having a pair of deep recesses 222a, 222b adjacent to its opposite ends is disposed in the upper region of the sideplates 221a, 221b. One of the recesses, 222a, receives a supply of clearing liquid 223a which is to be supplied to a specimen film 1, while the other recess 222b receives the same clearing liquid 223b which drips from the specimen film 1. Centrally, the vessel 222 is also formed with a shallow recess 222e in which a transparent glass plate 224 is embedded. In the region of the glass plate 224, a retaining plate 225 is placed thereon and has a transparent glass plate 226 fitted therein at a position opposite to the glass plate 24. The glass plates 224, 226 maintain a small clearance therebetween and form part of a feed path 1A for the specimen film 1.

A roller support box 231 is mounted on the pair of connecting rods 227, 228, by engaging notches 232a, 232b, 232c, 232d formed in the lower parts of the opposite ends of its two sidewalls 232a, 232b with these rods. Four pairs of mating feed rollers 233, 234; 235, 236; 237, 238; and 239, 240 are rotatably mounted on the sidewalls 231a, 231b of the box 231, the pair of rollers 235, 236 and the pair of rollers 237, 238 being located above the recesses 222a and 222b, respectively, of the liquid vessel 222, and the pair of rollers 233, 234 and the pair of rollers 239, 240 being located outwardly of the first mentioned pairs of rollers. The respective rollers define the feed path 1A for the specimen film 1 in conjunction with the glass plates 224, 226, and the roller 236 is partially immersed into the clearing liquid 223a contained in the recess 222a. The rollers 233, 235, 237 and 239 are mounted on shafts 233a, 235a, 237a and 239a, respectively, one end of which fixedly carries gears 241, 242, 243 and 244, respectively, as shown in FIG. 30. A chain 248 extends around these gears and also around a gear 247 (see FIG. 31) which is fixedly mounted on the shaft 245a of a continuous feed motor 245 which is in turn fixedly mounted on the top 231c of the box 231 by means of a support member 246.

A box 250 for supporting the light source unit is disposed below the liquid vessel 222 by slidably engaging the guide rods 258, 259 with a pair of mounting discs 260, 261 which are fitted into the opposite sidewalls 250a, 250b of the box 250. As shown in FIG. 29, the box 250 houses a lamp 251, a condenser lens 252a, a prism 253 and a group of condenser lenses 252b. Specifically, an illuminating light emanating from the lamp 251 is directed along an optical path $O_1$ defined by these optical members and projected upwardly through an exit pupil 252c for transmission through an elongate slot 222c which is formed in the lower sidewall of the vessel 222 in the region below the glass plate 224, and then through the glass plate 224, the specimen film 1 and the glass plate 226. It is to be noted that as viewed in FIG. 29, the slot 222c is elongate in a direction perpendicular to the plane of the drawing while it extends in the vertical direction as viewed in FIG. 30. An elongate slot 225a extending in the same direction as the slot 222c is formed in the portion of the retaining plate 225 which is located above the glass plate 226, and receives a light receiving portion of a photoelectric transducer element which is supported by a support plate 257a. A measuring port Co is defined at the intersection of the optical path $O_1$ of the illuminating light and the feed path 1A of the specimen film 1. A slot 225b is formed in a portion of the retaining plate 225 which is located in the upper, right-hand portion thereof, as viewed in FIG. 30, and receives a light receiving portion of a photoelectric transducer element 225 which is secured to the retaining plate 225 by means of a mounting plate 225a. In a region of the liquid vessel 222 which is located below the transducer element 225, there is formed a slot 222d as shown in FIG. 29, and a light emitting diode 254 is mounted on the liquid vessel 222 by means of a mounting member 232 so as to be located below the slot 222d. The combination of the transducer element 255 and the light emitting diode 254 is effective to detect a position mark (shown in FIGS. 33 to 36) on the specimen film 1 for controlling the operation of various parts of the apparatus.

As shown in FIG. 30, the support plate 257a for the transducer element 256 extends below the lower end of the sidewalls 231a, 231b of the roller support box 231, and then its opposite ends are bent laterally in opposite directions, where it is secured to a bracket 257b (see FIG. 29) which is secured to the top of the condenser lens assembly 252b, by means of set screws 221d, 221e (see FIG. 30).

The disc 260 which is secured to the box 250 supporting the light source unit and which is slidably mounted on the guide rod 258 is integrally formed with a rack 262, which meshes with a pinion 264 fixedly mounted on the output shaft 263a of a scan motor 263. The scan motor 263 is secured to the support plate 221c which is secured across both sideplates 221a, 221b of the apparatus 221. When the scan motor 263 is energized, the pinion 264 is rotated to drive the rack 262, which in turn causes the box 250 to be axially displaced along the guide rods 258, 259. A displacement of the box 250 in this direction also causes a displacement of the transducer element 256 in the same direction, thus scanning the specimen film 1.

Figure 31:
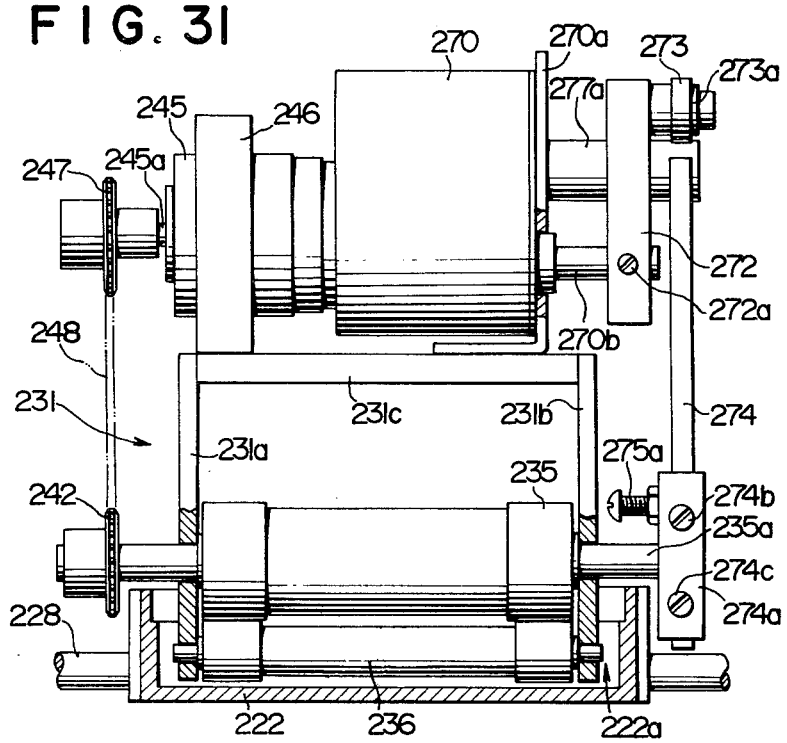
Figure 32:
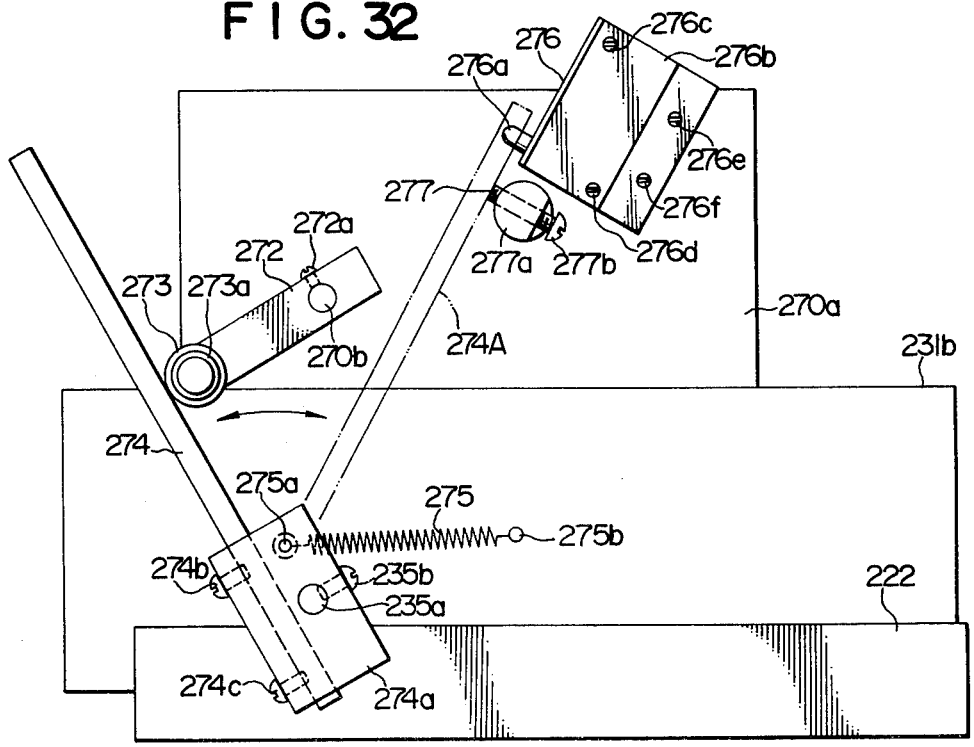

In addition to the continuous feed motor 245, an intermittent feed motor 270 is fixedly mounted on the top 231c of the roller support box 231 by means of a mounting plate 270a, as shown in FIG. 31. The motor 270 has an output shaft 270b on which one end of an arm member 272 is fitted and secured thereto by a set screw 272a. The free end of the arm member 272 carries a pressure roller 273 which is pivotally mounted at 273a. A mounting member 274a is fitted on the right-hand end, as viewed in FIG. 31, of the shaft 235a associated with the feed roller 235, and is integrally secured thereto by a set screw 235b (see FIG. 32). A rocking arm 274 is fitted into the mounting member 274a and is integrally secured thereto by a pair of set screws 274b, 274c. It is to be noted that the feed roller 235 and the shaft 235a are interconnected by one way rotational clutch, not shown, such that the connection therebetween is only effective in a direction to feed the specimen film 1 to the right, as viewed in FIG. 29.

The free end of the rocking arm 274 is located on a path of rotation of the roller 273 carried by the arm member 272, and is normally biased by a spring 275 (see FIG. 32), extending between a pin 275a fixedly mounted on the mounting member 274a and another pin 275b mounted on one wall 231b of the roller support box 231, into a position 274A shown in phantom line, in which it bears against a stop 277, thus pressing against the actuator 276a of a microswitch 276. The stop 277 threadably engages a support rod 277a which is fixedly mounted on the mounting plate 270a of the motor 270, and the position at which it bears against the rocking arm 274 can be adjusted by turning its head 277b. The microswitch 276 is secured to a support plate 276b by a pair of set screws 276c, 276d which support plate 276b is secured to the mounting plate 270a by means of a pair of set screws 276e, 276f.

In operation, the specimen film 1 which is dyed, decolorized and dried is loaded into the apparatus 221 from the left-hand side, as viewed in FIG. 29, and the continuous feed motor 245 is set in motion, whereby the four pairs of feed rollers 233, 234; 235, 236; 237, 238; 239, 240 are simultaneously driven to rotate through the chain 248. The rotation of these rollers is effective to feed the specimen film 1 from left to right, as viewed in FIG. 29. During such movement, when the film 1 passes between the rollers 235 and 236, the clearing liquid 223a is applied to the film 1 by the roller 236 which is partially immersed into such liquid, whereby the film 1 is uniformly made clear. The application of the clearing liquid to the film can be assured by using a hygroscopic material such as sponge for the roller 236. As the film 1 is fed further to the right, it is fed into the space between the pair of transparent glass plates 224, 226, moving therethrough. When the leading end of the film reaches a position between the light emitting diode 254 and the transducer element 255, there occurs a change in the amount of light reaching the latter, whereby a signal is produced to interrupt the operation of the continuous feed motor 245, holding the film at the position which it then occupies. Since the film 1 is made clear by the liquid 223a by this time, the change in the amount of light may be reduced, making the detection difficult. To overcome this difficulty, it is desirable that the leading portion of the film 1 be provided with an opaque position mark. When the film 1 is stopped at a given position in this manner, the scan motor 263 is set in motion, whereby the pinion 264 and the rack 262 causes the box 250 supporting the light source unit, which has its exit pupil 252c positioned laterally of the specimen film 1 initially, to be displaced at the measuring port Co in a direction to traverse the film 1, or in the vertical direction as viewed in FIG. 30. As the box 250 is displaced in this manner, the support plate 257a for the transducer element 256 is also moved integrally therewith. As a result, the specimen film 1 is scanned by an illuminating light emanating from the lamp 251 while remaining at the given position, and the light which is transmitted through the foremost specimen is received by the transducer element 256 for utilization by a measuring device, not shown. The position of the transducer element 255 and the light emitting diode 254 as well as the exit pupil 252c in the box 250 is chosen in correct alignment with the pitch P (see FIG. 38) of the specimens on the film 1 so that the fractionated pattern of the foremost specimen is aligned with the optical path of the illuminating light, thus assuring an accurate scanning of the fractionated pattern. The fractionated pattern of the specimen as detected by the transducer element 256 is recorded by a suitable recorder, not shown. When the determination of one fractionated pattern of the blood serum is completed, the scan motor 263 is driven in the opposite direction as by a suitably located limit switch, thereby returning the box 250 and the transducer element 256 to their original positions. At the same time, the intermittent feed motor 270 is set in motion, whereby the arm member 272 is rotated to drive the feed roller 235 and hence the four pairs of feed rollers which are operationally connected therewith through the chain 248 by a given increment. In this manner, the film 1 is fed by one pitch, whereby the fractionated pattern of a second specimen is located at the measuring port Co. Thereupon, the scan motor 263 is again set in motion for determination of the density of the fractionated pattern of the second specimen. In this manner, the fractionated pattern of individual specimens applied to the film 1 is successively determined and when the determination has been completed for all of the specimens, the continuous feed motor 245 is again set in motion to deliver the film 1 externally of the apparatus 221. Any amount of clearing liquid 223b which may drip from the film during the measurement or during the feeding operation, for example, during its passage between the rollers 237, 238, is received in the recess 222b of the liquid vessel 222.

Figure 33:
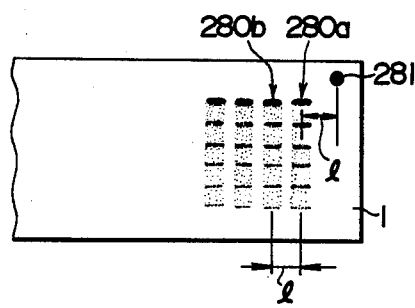
FIGS. 33 to 36 are plan view of specimen serum bearing films having position marks.
Figure 34:
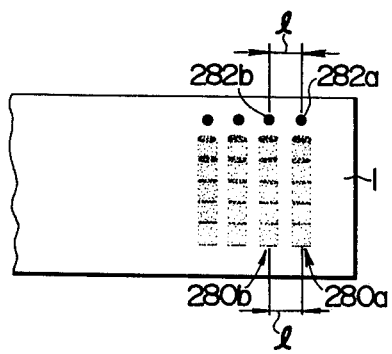
Figure 35:
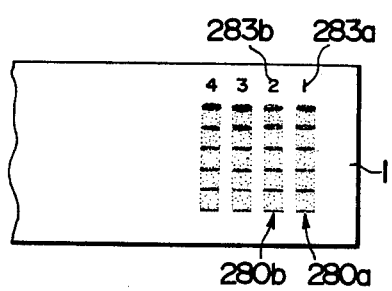
Figure 36:
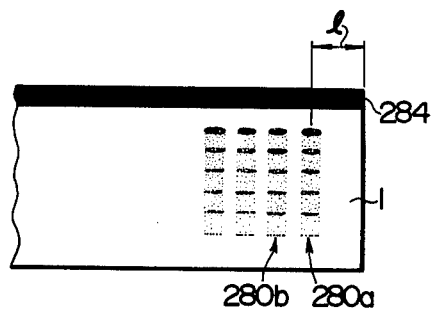

FIGS. 33 to 36 show several examples of the position mark or marks. In FIG. 33, the film is formed with fractionated serum patterns 280a, 280b . . . at an equal spacing l as a result of the cataphoresis, dyeing, decolorization and drying steps. A position mark 281 is printed on the film at the distance l to the right of the rightmost or first pattern 280a to be determined. In FIG. 34, a plurality of position marks 282a, 282b . . . are printed in alignment with the fractionated patterns 280a, 280b . . . In FIG. 35, a plurality of specimen numbers 283a, 283b . . . are marked in alignment with the respective patterns and are utilized as position marks. In FIG. 36, a continuous strip-like mark 284 of a constant width is applied lengthwise of the film along one lateral edge thereof.

In use of the film shown in FIG. 33, when the leading end of the film 1 has passed the light emitting element 254 and the position mark 281 reaches the latter, the transducer 255 detects it and produces a signal which may be utilized to stop the motion of the feed motor. With a film of the type shown in FIG. 34, the element 254 and the transducer 255 may be located in alignment with the path of movement of the marks 282. Each time one of these marks is detected, the feed motion of the film is interrupted and the respective fractionated pattern scanned. This permits a proper scanning if the serum of the respective specimens is not applied at an equal interval. With a film of the type shown in FIG. 35, the numeral of the position mark allows the respective specimens to be identified. The film of FIG. 36 is detected by the combination of elements 254, 255 when its leading edge reaches the position between them. These position marks may be applied simultaneously with the application of the serum to the film, by providing a suitable marker on the serum application member shown in FIG. 7.

Figure 37:
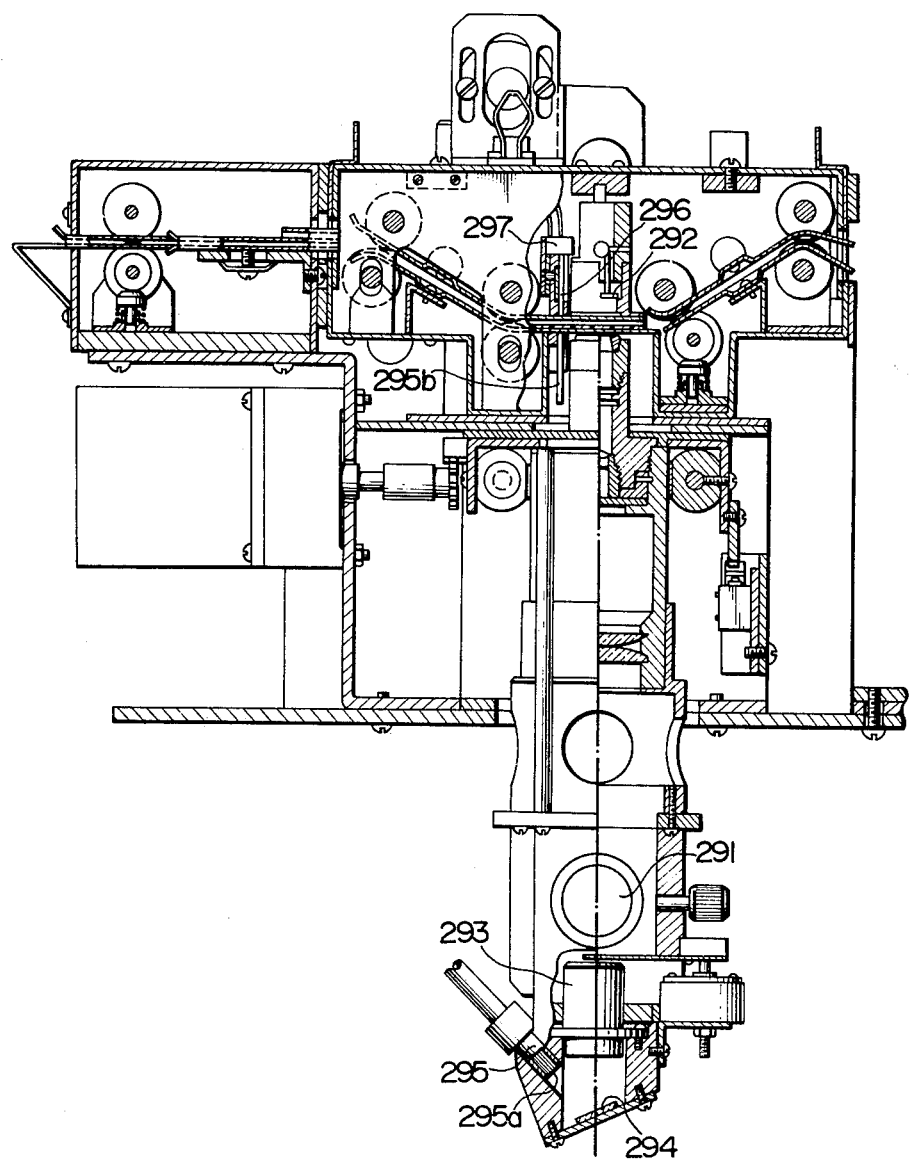
FIG. 37 is a view showing another form of densitometer.

FIG. 37 shows another embodiment of the densitometer which includes a similar arrangement to the previous embodiment for the film feeding, photometry and scanning, but which employs a different positioning mechanism. The previous embodiment shown in FIGS. 29 to 32 employed the light emitting element and the light receiving element for the purpose of positioning. However, in the present embodiment, a light source provided for the photometric is connected through an optical fibre to provide a positioning light source. This aspect will be described with reference to FIG. 37. A light source is shown at 291 and supplies light to a photometric light receiving element 292. A condenser lens 293 is disposed adjacent to the source 291 to direct light from the source 291 to a reflecting mirror 294, and an optical fibre bundle 295 is disposed so that its one end face 295a is capable of receiving reflected light from the mirror 294. The opposite end 295b of the fibre bundle is disposed at right angles to the path of movement of the film so that individual fibres emit light in a direction perpendicular to the film. Light passing through the film impinges on a plurality of fibres of a bundle 296 which are disposed on the opposite side of the film at right angles to the film surface. The fibre bundle 296 leads to a positioning light receiving element 297.

In operation, when the film is fed by rollers from left to right, as viewed in this Figure, into immersion into the clearing liquid, its leading end is located between the end 295b of the fibre bundle 295 and the fibre bundle 296, causing a change in the amount of light reaching the element 297 to enable the detection of the position. While in the previous embodiment, the positioning light receiving element was located to the right, as viewed in FIG. 27, or forwardly in the direction of movement of the film, it is located to the left or rearwardly of the photometric element, and hence it is evident that the feeding motion of the film will have to be interrupted a given time interval after the detection of the film by the element 297. The use of optical fibres enables more positive detection of the film position, since the full width rather than a single point of the film is subject to the detection.

What is claimed is:

1. An apparatus for examining and analyzing blood serum samples deposited on a strip of film, wherein said film strip bearing blood serum is cataphoretically processed and is carried into one side of the apparatus, comprising means for feeding said film strip along a predetermined path through a photometry location having a film receiving side and a film exiting side, said photometry location including a light source and a photoelectric transducer for photometry of the density distribution of a fractionated pattern of the blood serum, positioning apparatus disposed on the film receiving side of said photometry location and including a positioning photoelectric transducer for producing a detecting signal in response to said fractionated pattern passing said positioning transducer, means responsive to said detecting signal for stopping the feeding of said film strip at said photometry location where said photometry transducer scans said fractionated pattern to perform a photometry analysis, said positioning apparatus further including a first optical fiber bundle having a first end face positioned to receive light from said light source and a second opposite end face adjacent to said path constructed and arranged so that the width of said first bundle is substantially equal to the width of said film strip, and a second optical fiber bundle for transmitting the light which passes through said film strip to said positioning photoelectric transducer, said second optical fiber bundle having a first end face positioned opposite to the second end face of said first bundle with said film strip moving therebetween and a second end face positioned adjacent to said positioning transducer.

* * * * *

UNITED STATES PATENT AND TRADEMARK OFFICE
CERTIFICATE OF CORRECTION

PATENT NO. : 4,204,767
DATED : May 27, 1980
INVENTOR(S) : Yutaka Kato, et al

It is certified that error appears in the above—identified patent and that said Letters Patent is hereby corrected as shown below:

Column 3, line 56, change "13" to --3--.

Column 4, line 62, change "slot" to --slots--.

Column 9, line 11, change "rotor" to --motor--.

Column 15, line 1, change "ffect" to --effect--.

Column 15, line 19, change "24" to --224--.

Signed and Sealed this

Eighth Day of September 1981

[SEAL]

Attest:

GERALD J. MOSSINGHOFF

Attesting Officer    Commissioner of Patents and Trademarks